US008101193B2

(12) United States Patent
Aagaard et al.

(10) Patent No.: US 8,101,193 B2
(45) Date of Patent: *Jan. 24, 2012

(54) TUBERCULOSIS VACCINES COMPRISING ANTIGENS EXPRESSED DURING THE LATENT INFECTION PHASE

(75) Inventors: Claus Aagaard, Copenhagen (DK); Carina Vingsbo-Lundberg, Hollviken (SE); Peter Andersen, Bronshoj (DK)

(73) Assignee: Statens Serum Institut, Copenhagen S (DK)

( * ) Notice: Subject to any disclaimer, the term of this patent is extended or adjusted under 35 U.S.C. 154(b) by 0 days.

This patent is subject to a terminal disclaimer.

(21) Appl. No.: 13/101,980

(22) Filed: May 5, 2011

(65) Prior Publication Data

US 2011/0206713 A1 Aug. 25, 2011

Related U.S. Application Data

(63) Continuation of application No. 11/993,199, filed as application No. PCT/DK2006/000356 on Jun. 20, 2006, now Pat. No. 7,968,105.

(30) Foreign Application Priority Data

Jun. 23, 2005 (DK) .................................. 2005 00924
Oct. 5, 2005 (DK) .................................. 2005 01393

(51) Int. Cl.
*A61K 39/04* (2006.01)
*A61K 39/02* (2006.01)
*C07H 21/04* (2006.01)

(52) U.S. Cl. ..... 424/248.1; 424/9.1; 424/9.2; 424/185.1; 424/234.1; 530/300; 530/350; 536/23.1; 536/23.7

(58) Field of Classification Search .................... 424/7.1, 424/7.2, 185.1, 234.1, 248.1; 530/300, 350; 536/23.1, 23.7
See application file for complete search history.

(56) References Cited

U.S. PATENT DOCUMENTS

| 6,485,914 B1 | 11/2002 | Izutsu et al. |
| 6,641,814 B1 | 11/2003 | Andersen et al. |

FOREIGN PATENT DOCUMENTS

| WO | WO 01/23388 A2 | 4/2001 |
| WO | WO 01/79274 A2 | 10/2001 |
| WO | WO 03/004520 A2 | 1/2003 |
| WO | WO 2004/006952 A2 | 1/2004 |
| WO | WO 2004/083448 A2 | 9/2004 |

OTHER PUBLICATIONS

Agger E. M. et al., "Protective immunity to tuberculosis with Ag85B-ESAT-6 in a synthetic cationic adjuvant system IC31" Vaccine, Butterworth Scientific. Guildford, GB, vol. 24, No. 26, Jun. 29, 2006, pp. 5452-5460.

Andersen, P. et al., "Simultaneous electroelution of whole SDS-polyacrylamide gels for the direct cellular analysis of complex protein mixtures" 1993, J. Immunol. Methods 161, pp. 29-39.
Andersen, P. et al., "Proteins Released from *Mycobacterium tuberculosis* during Growth" 1991, Infect. Immun. 59, pp. 1905-1910.
Betts, J. et al., "Evaluation of a nutrient starvation model of *Mycobacterium tuberculosis* persistence by gene and protein expression profiling" 2002, Molecular Microbiology, 43, pp. 717-731.
Brandt, L. et al., "ESAT-6 Subunit Vaccination against *Mycobacterium tuberculosis*" 2000 Infect. Immun. 68:2, pp. 791-795.
Brooks, J.V., et al., "Boosting Vaccine for Tuberculosis" Infect. Immun 2001, 69(4), pp. 2714-2717.
Colditz, G.A., et al., "Efficacy of BCG Vaccine in the Prevention of Tuberculosis" JAMA 1994, 271, pp. 698-702.
Cole, S.T. et al., "Deciphering the biology of *Mycobacterium tuberculosis* from the complete genome sequence" 1998 Nature 393, pp. 537-544.
Cote-Sierra J. et al., "A new membrane-bound Oprl lipoprotein expression vector High production of heterologous fusion proteins in Gram (−) bacteria and the implications for oral vaccination" 1998, Gene Oct. 9, 221(1), pp. 25-34.
Dietrich J. et al., "Exchanging ESAT6 with TB10.4 in an Ag85B Fusion Molecule-Based Tuberculosis Subunit Vaccine: Efficient Protection and ESAT6-Based Sensitive Monitoring of Vaccine Efficacy" Journal of immunology, vol. 174, No. 10, May 2005, pp. 6332-6339.
Gosselin, E. et al., "Enhanced Antigen Presentation using Human Fcy Receptor (Monocyte/Macrophage)-Specific Immunogens" 1992, J. Immunol. 149, pp. 3477-3481.
Harboe, M. et al., "B-Cell Epitopes and Quantification of the ESAT-6 Protein of *Mycobacterium tuberculosis*" 1998, Infect. Immun. 66:2, pp. 717-723.
Kilgus J. et al., "Analysis of the Permissive Association of a Malaria T Cell Epitope with DR Molecules" J. Immunol., Jan. 1, 1991, 146(1), pp. 307-315.
Köhler G. et al., "Continuous cultures of fused cells secreting antibody of predefined specificity" Nature, 1975, 256, pp. 495-497.
Leyten E. et al., "Human T-cell responses to 25 novel antigens encoded by genes of the dormancy regulon of *Mycobacterium tuberculosis*" Microbes and Infection, Elsevier, Paris, FR, vol. 8, No. 8, Jul. 2006, pp. 2052-2060.
Lowrie, D.B. et al., "Therapy of tuberculosis in mice by DNA vaccination" 1999, Nature, 400, pp. 269-271.
Lustig J.V. et al., "Humoral and Cellular Responses to Native Antigen following Oral and Parenteral Immunization with Lipid-Conjugated Bovine Serum Albumin" 1976, Cell Immunol. 24(1), pp. 164-172.
Lyashchenko, K.P. et al., "A multi-antigen print immunoassay for the development of serological diagnosis of infectious diseases" 2000, J. Immunological Methods 242, pp. 91-100.

(Continued)

*Primary Examiner* — Rodney P. Swartz
(74) *Attorney, Agent, or Firm* — Knobbe Martens Olson & Bear LLP

(57) ABSTRACT

The invention is related to an immunogenic composition, vaccine or pharmaceutical composition for preventing, boosting or treating infection caused by a species of the *tuberculosis* complex (*M. tuberculosis, M. Bovis, M. africanum, M. microti*). The immunogenic composition, vaccine or pharmaceutical composition comprise a fusion polypeptide, which comprises one or more starvation antigens from *M. tuberculosis*, the units of the fusion polypeptide being *M. tuberculosis* antigens. Further, the invention is related to the use of a vaccine comprising a fusion polypeptide sequence or nucleic acid sequence of the invention given at the same time as BCG, either mixed with BCG or administered separately at different sites or routes for preparing said immunogenic composition, vaccine, or pharmaceutical composition.

18 Claims, 8 Drawing Sheets

OTHER PUBLICATIONS

Figure 1:
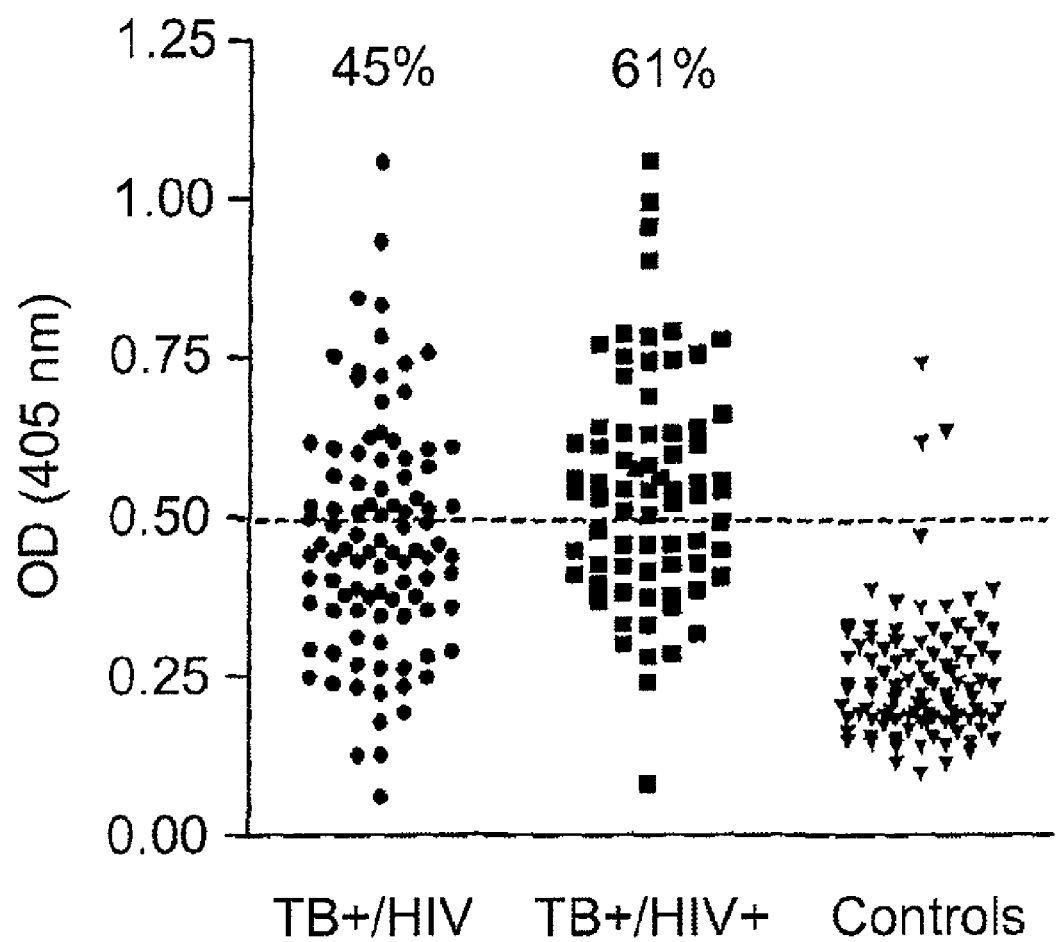

McCafferty J. et al., "Phage antibodies: filamentous phage displaying antibody variable domains" 1990, Nature, 348, pp. 552-554.

Merrifield, R.B., "Solid Phase Peptide Synthesis. I. The Synthesis of a Tetrapeptide" 1963, J. Am. Chem. Soc. 85 (14), pp. 2149-2154.

Merrifield, R.B. "Peptide Synthesis on a Solid Polymer" Fed. Proc. Am. Soc. Ex. Biol., 1962, p. 412, vol. 21.

Mowat, A.M. et al., "Immune-stimulating complexes containing Quil A and protein antigen prime class I MHC-restricted T lymphocytes in vivo and are immunogenic by the oral route" 1991, Immunology 72(3), pp. 317-322.

Nagai, S. et al., "Isolation and Partial Characterization of Major Protein Antigens in the Culture Fluid of *Mycobacterium tuberculosis*" 1991, Infect. Immun. 59:1, pp. 372-382.

Olsen A. W. et al., "Efficient protection against *Mycobacterium tuberculosis* by vaccination with a single subdominant epitope from the ESAT-6 antigen" Eur. J. Immunol. Jun. 2000 30(6), pp. 1724-1732.

Olsen A. W. et al., "Protection of Mice with a Tuberculosis Subunit Vaccine Based on a Fusion Protein of Antigen 85B and ESAT-6" Infection and Immunity, American Society for Microbiology, vol. 69, No. 5, May 2001, pp. 2773-2778.

Pearson W.R. et al., "Improved tools for biological sequence comparison" 1988, PNAS USA 85, pp. 2444-2448.

Pollock, J. et al., "Assessment of defined antigens for the diagnosis of bovine tuberculosis in skin test-reactor cattle" 2000, The Veterinary record, 146, pp. 659-665.

Ravn, P. et al., "Human T Cell Responses to the ESAT-6 Antigen from *Mycobacterium tuberculosis*" 1999, J. Infect. Dis. 179, pp. 637-645.

Rolph, M.S. et al., "Recombinant viruses as vaccines and immunological tools" 1997, Curr. Opin. Immunol. 9, pp. 517-524.

Rosenkrands, I. et al., "Identification and Characterization of a 29-Kilodalton Protein from *Mycobacterium tuberculosis* Culture Filtrate Recognized by Mouse Memory Effector Cells" 1998, Infect. Immun. 66:6, pp. 2728-2735.

Sherman, D.R. et al., Regulation of the *Mycobacterium tuberculosis* hypoxic response gene encoding alpha-crystallin 2001 Proc Natl Acad Sci USA 98, pp. 7534-7539.

Sinigaglia, F. et al., "A malaria T-cell epitope recognized in association with most mouse and human MHC class II molecules" Nature, Dec. 22-29, 1988, 336(6201), pp. 778-780.

Skjot, R.L.V. et al., "Comparative Evaluation of Low-Molecular-Mass Proteins from *Mycobacterium tuberculosis* Identifies Members of the ESAT-6 Family as Immunodominant T-Cell Antigens" 2000, Infect. Immun. 68:1, pp. 214-220.

Stryhn, A. et al., "Peptide binding specificity of major histocompatibility complex class I resolved into an array of apparently independent subspecificities: quantitation by peptide libraries and improved prediction of binding" 1996 Eur. J. Immunol. 26, pp. 1911-1918.

Thompson J. et al., "Clustal W: Improving the sensitivity of progressive multiple sequence alignment through sequence weighting, position-specific gap penalties and weight matrix choice" Nucleic Acids Res. 1994, 22, pp. 4673-4680.

Theisen, M., et al., "Antigenicity and Immunogenicity of Recombinant Glutamate-Rich Protein of *Plasmodium falciparum* Expressed in *Escherichia coli*" 1995, Clin. Diagn. Lab. Immunol. 2(1), pp. 30-34.

Turner, Joanne et al., "Effective Preexposure Tuberculosis Vaccines Fail to Protect When They Are Given in an Immunotherapeutic Mode" Infection and Immunity, Mar. 2000, p. 1706-1709, vol. 68, No. 3.

Ulmer, Jeffrey B. et al., "Toward the development of DNA vaccines" Current Opinion in Biotechnology, 1996, pp. 653-658, vol. 7.

Ulmer, Jeffrey B. et al., "DNA vaccines" Current Opinion in Biotechnology, 1996, pp. 531-536, vol. 8.

Database UniProt, "Subname:Full=Putative uncharacterized protein" Feb. 1, 1997, XP002563173.

Database UniProt, "Subname:Full=Putative uncharacterized protein Mb2678c;" Oct. 1, 2003, XP002563174.

TUBERCULOSIS VACCINES COMPRISING ANTIGENS EXPRESSED DURING THE LATENT INFECTION PHASE

CROSS REFERENCE TO RELATED APPLICATIONS

This application is a continuation of and claims priority under 35 U.S.C. §120 to U.S. patent application Ser. No. 11/993,199, now U.S. Pat. No. 7,968,105, filed Jul. 25, 2008, which claims priority to and is a U.S. National Phase filing of PCT International Application Number PCT/DK2006/000356, filed on Jun. 20, 2006, designating the United States of America and published in the English language, which claims priority under 35 U.S.C. §119 to Denmark Patent Application Number PA 2005 01393 filed on Oct. 5, 2005, and Denmark Patent Application Number PA 2005 00924 filed on Jun. 23, 2005. The disclosures of the above-described applications are hereby expressly incorporated by reference in their entireties.

REFERENCE TO SEQUENCE LISTING

The present application is being filed along with a sequence listing in electronic format. The sequence listing is provided as a file entitled PLOUG8.003C1.txt, created May 5, 2011 which is 20.5 KB in size. The information in the electronic format of the sequence listing is incorporated herein by reference in its entirety.

FIELD OF INVENTION

The present invention discloses starvation induced antigens or new fusion polypeptides of immunogenic polypeptides based on polypeptides derived from *Mycobacterium tuberculosis* induced during starvation, the use of one or more of the fusion polypeptides or starvation induced antigens of the invention for the preparation of an immunogenic composition, vaccine or pharmaceutical composition to be used for administration to a person/animal and the immunogenic compositions, vaccines or pharmaceutical compositions as such.

GENERAL BACKGROUND

Human *tuberculosis* caused by *Mycobacterium tuberculosis* (*M. tuberculosis*) is a severe global health problem, responsible for approximately 3 million deaths annually, according to the WHO. The worldwide incidence of new *tuberculosis* (TB) cases had been falling during the 1960s and 1970s but during recent years this trend has markedly changed in part due to the advent of AIDS and the appearance of multidrug resistant strains of *M. tuberculosis*.

The only vaccine presently available for clinical use is BCG, a vaccine whose efficacy remains a matter of controversy. BCG generally induces a high level of acquired resistance in animal models of TB, and in humans it is protective against disseminated forms of *tuberculosis* such as meningitis and miliary *tuberculosis*. When given to young children it is protective against *tuberculosis* for years but then the efficacy wanes. Comparison of various controlled trials revealed that the protective efficacy of BCG in adults varied dramatically with an efficacy range from ineffective to 80% protection. This makes the development of a new and improved vaccine against *M. tuberculosis* an urgent matter, which has been given a very high priority by the WHO.

Many attempts to define protective mycobacterial substances have been made, and different investigators have reported increased resistance after experimental vaccination. *M. tuberculosis* holds, as well as secretes, several proteins of potential relevance for the generation of a new *M. tuberculosis* vaccine. The search for candidate molecules has primarily focused on proteins released from dividing bacteria. Despite the characterization of a large number of such proteins only a few of these have been demonstrated to induce a protective immune response as subunit vaccines in animal models, most notably ESAT-6 and Ag85B (Brandt et al 2000). However, the demonstration of a specific long-term protective immune response with the potency of BCG or the capability of boosting in a BCG vaccinating person has not yet been achieved. At best, boost of BCG with BCG has no effect [Colditz, 1994]. Boosting of BCG has been done with Ag85A(Brooks et al IAI 2001; WO0204018) in an inbred mouse strain leading to some protection, although compared to BCG alone it was not significantly better. Since BCG needs to divide and secrete proteins in order to induce a protective immune response, the lack of booster effect is primarily due to either sensitization with environmental mycobacteria or a residual immune response from the primary BCG vaccination. Both events lead to a rapid immune response against BCG and therefore quick inhibition of growth and elimination of BCG.

The course of a *M. tuberculosis* infection runs essentially through 3 phases. During the acute phase, the bacteria proliferate in the organs, until the immune response increases. Specifically sensitized CD4 T lymphocytes mediate control of the infection, and the most important mediator molecule seems to be interferon gamma (IFN-gamma). The bacterial loads starts to decline and a latent phase is established where the bacterial load is kept stable at a low level. In this phase *M. tuberculosis* goes from active multiplication to dormancy, essentially becoming non-replicating and remaining inside the granuloma. In some cases, the infection goes to the reactivation phase, where the dormant bacteria start replicating again. It has been suggested that the transition of *M. tuberculosis* from primary infection to latency is accompanied by changes in gene expression (Honer zu Bentrup, 2001). It is also likely that changes in the antigen-specificity of the immune response occur, as the bacteria modulates gene expression during its transition from active replication to dormancy. The full nature of the immune response that controls latent infection and the factors that lead to reactivation are largely unknown. However, there is some evidence for a shift in the dominant cell types responsible. While CD4 T cells are essential and sufficient for control of infection during the acute phase, studies suggest that CD8 T cell responses are more important in the latent phase.

In 1998 Cole et al published the complete genome sequence of *M. tuberculosis* and predicted the presence of approximately 4000 open reading frames (Cole et al 1998) disclosing nucleotide sequences and putative protein sequences. However importantly, this sequence information cannot be used to predict if the DNA is translated and expressed as proteins in vivo. It is known that some genes of *M. tuberculosis* are upregulated under conditions that mimic latency. However, these are a limited subset of the total gene expression during latent infection. Moreover, as one skilled in the art will readily appreciate, expression of a gene is not sufficient to make it a good vaccine candidate. The only way to determine if a protein is recognized by the immune system during latent infection with *M. tuberculosis* is to produce the given protein and test it in an appropriate assay as described herein. A number of proteins are of particular importance and have potential for being late antigens (antigens recognized during latent infection) since they are mainly expressed a relatively long time after infection where the immune system has mounted the first adaptive defense and the environment has turned more hostile for the mycobacteria. In vitro hypoxic culture conditions, which mimic the conditions of low oxygen tension have previously been suggested as relevant in this regard and have been used to analyze changes in gene expression. A number of antigens have been found that are induced or markedly upregulated under these conditions e.g. the 16 kDa antigen α-crystalin (Sherman 2001), Rv2660c and Rv2659c (Betts, 2002). (our own application) Another environmental stimuli which may be of particular interest is starvation designed to reflect that nutrients are restricted in the granuloma (the location of the latent infection) and that products expressed by genes upregulated under starvation therefore may be of particular interest as antigen targets during the latent stage of infection.

Of the more than 200 hundred antigens known to be expressed during primary infection, and tested as vaccines, less than a half dozen have demonstrated significant potential. So far only one antigen has been shown to have any potential as a therapeutic vaccine (Lowrie, 1999). However this vaccine only worked if given as a DNA vaccine and has proved controversial, with other groups claiming that vaccination using this protocol induces either non-specific protection or even worsens disease (Turner, 2000). In contrast, the fusion polypeptides described in the invention may be incorporated in a vaccine that use well-recognized vaccination technology, as demonstrated in provided examples.

Further, since TB vaccines do not result in sterilizing immunity but rather control the infection at a subclinical level (thereby resulting in the subsequent establishment of latent infection), a multiphase vaccine which combines components with prophylactic and therapeutic activity is described in this invention. After conventional prophylactic vaccination, the evasion of the primary immune response and the subsequent development of latent disease is probably at least in part due to the change in the antigenic profile of the invading bacteria. Thus, vaccinating with antigens associated with latent TB should prevent or reduce the establishment of latent infection and therefore, a vaccine incorporating antigens expressed by the bacteria both in the first logarithmic growth phase and during latent disease should improve long-term immunity when used as a prophylactic vaccine. Such a multiphase vaccine will obviously also be efficient as a therapeutic vaccine thereby addressing the problem that the majority of the population in the third world who would receive a future TB vaccine would be already latently infected.

SUMMARY OF THE INVENTION

The invention is related to an immunogenic composition, vaccine or pharmaceutical composition for preventing (including booster vaccination and multiphase vaccines) or/and treating infection caused by a species of the *M. tuberculosis* complex (*M. tuberculosis*, *M. Bovis*, *M. africanum* etc.), the immunogenic composition, the vaccine or pharmaceutical composition comprising starvation induced antigen or a fusion polypeptide which comprises one or more starvation induced *M. tuberculosis* antigens, the units of the fusion polypeptide being *M. tuberculosis* antigens. Also, the invention relates to the fusion polypeptides as such and to a nucleic acid sequence encoding such a fusion polypeptide. Further, the invention relates to the use of short or long overlapping or non-overlapping peptide(s) made synthetically or recombinant. Further, the invention relates to the use of a starvation induced antigen or a fusion polypeptide sequence or nucleic acid sequence of the invention for preparing said immunogenic composition, vaccine, or pharmaceutical composition and the vaccine or pharmaceutical composition produced in this way. Further, the invention relates to the use of a vaccine comprising a starvation induced antigen or a fusion polypeptide sequence or nucleic acid sequence of the invention given at the same time as BCG, either mixed with BCG or administered separately at different sites or routes for preparing said immunogenic composition, vaccine, or pharmaceutical composition. Further the invention relates to the use of a vaccine comprising a starvation induced antigen or a fusion polypeptide sequence or nucleic acid sequence given as a BCG booster. Furthermore, by including antigens that are expressed both early and late during a natural infection the vaccine will lead to a two step immune response allowing the immune system to combat the pathogen with whatever epitopes are most efficient at a certain timepoint including during latency.

DETAILED DISCLOSURE OF THE INVENTION

The present invention discloses immunogenic compositions, a vaccine or a pharmaceutical composition comprising a starvation induced antigen or a fusion polypeptide comprising one or more starvation induced antigens.

The amino acid and nucleic acid sequences of these starvation induced (more than 6.5 fold upregulated during starvation or genetically linked to a starvation induced gene) antigens appear from the sequence listing as follows:

| Starvation induced antigen | DNA SEQ ID NO | aa SEQ ID NO |
|---|---|---|
| Rv2655 | 1 | 2 |
| Rv2656 | 3 | 4 |
| Rv2657 | 5 | 6 |
| Rv2658 | 7 | 8 |
| Rv2659c | 9 | 10 |
| Rv2660c | 11 | 12 |
| Rv2661 | 13 | 14 |
| Rv2662 | 15 | 16 |
| Rv2663 | 17 | 18 |
| Rv0188 | 19 | 20 |
| Rv3290c | 21 | 22 |
| Rv3289c | 23 | 24 |
| Rv2034 | 25 | 26 |
| Rv2169c | 27 | 28 |
| Rv0116c | 29 | 30 |
| Rv2558 | 31 | 32 |
| Rv1152 | 33 | 34 |
| Rv3291c | 35 | 36 |
| Rv1284 | 37 | 38 |
| Rv1954c | 39 | 40 |
| Rv3810 | 41 | 42 |
| Rv2517c | 43 | 44 |
| Rv3288c | 45 | 46 |
| Rv0789c | 47 | 48 |
| Rv1955 | 49 | 50 |
| Rv3735 | 51 | 52 |
| Rv3675 | 53 | 54 |
| Rv2270 | 55 | 56 |
| Rv2050 | 57 | 58 |
| Rv3287c | 59 | 60 |
| Rv2557 | 61 | 62 |
| Rv0122 | 63 | 64 |
| Rv2497c | 65 | 66 |
| Rv1250 | 67 | 68 |
| Rv1552 | 69 | 70 |
| Rv2526 | 71 | 72 |
| Rv1809 | 73 | 74 |
| Rv0918 | 75 | 76 |
| Rv0516c | 77 | 78 |
| Rv2745c | 79 | 80 |
| Rv1472 | 81 | 82 |
| Rv1660 | 83 | 84 |
| Rv2302 | 85 | 86 |

In the present context the individual immunogenic polypeptide based on polypeptides derived from *M. tuberculosis* is termed a "unit" of the fusion polypeptide. The fusion may comprise 2, 3, 4, 5, 6, 7, 8, 9 or even 10 different units.

The order of the units of the fusion polypeptide can be any combination. In order terms, fusion polypeptides of all of the above antigens in any combination are within the scope of the present invention. The fusion polypeptides of the invention are useful for the preparation of an immunogenic composition, vaccine or pharmaceutical composition, in particular a BCG booster vaccine, as will be described in detail in the following.

The preferred polypeptides making up units of the fusion polypeptides together with the starvation polypeptides have the following Sanger identity number and amino acid sequences:

| Trivial name | Sanger ID |
|---|---|
| ESAT6 | Rv3875 |
| TB10.4 | Rv0288 |
| Ag85A | Rv3804c |
| Ag85B | Rv1886c |
| ORF2c | Rv3871 (c-terminal) |
| TB13.0 | Rv1036 |
| TB9.56 | Rv0285 |
| TB9.8 | Rv0287 |

| Polypeptide | amino acid sequence | aa SEQ ID NO |
|---|---|---|
| ESAT6 | MTEQQWNFAG IEAAASAIQG NVTSIHSLLD EGKQSLTKLA AAWGGSGSEA YQGVQQKWDA TATELNNALQ NLARTISEAG QAMASTEGNV TGMFA | 87 |
| Ag85A | SRGPLP VEYLQVPSPS MGRDIKVQFQ SGGANSPALY LLDGLRAQDD FSGWDINTPA FEWYDQSGLS VVMPVGGQSS FYSDWYQPAC GKAGCQTYKW ETFLTSELPG WLQANRHVKP TGSAVVGLSM AASSALTLAI YHPQQFVYAG AMSGLLDPSQ AMGPTLIGLA MGDAGGYKAS DMWGPKEDPA WQRNDPLLNV GKLIANNTRV WVYCGNGKPS DLGGNNLPAK FLEGFVRTSN IKFQDAYNAG GGHNGVFDFP DSGTHSWEYW GAQLNAMKPD LQRALGATPN TGPAPQGA | 88 |
| Ag85B | SRPGLPVEY LQVPSPSMGR DIKVQFQSGG NNSPAVYLLD GLRAQDDYNG WDINTPAFEW YYQSGLSIVM PVGGQSSFYS DWYSPACGKA GCQTYKWETF LTSELPQWLS ANRAVKPTGS AAIGLSMAGS SAMILAAYHP QQFIYAGSLS ALLDPSQGMG PSLIGLAMGD AGGYKAADMW GPSSDPAWER NDPTQQIPKL VANNTRLWVY CGNGTPNELG GANIPAEFLE NFVRSSNLKF QDAYNAAGGH NAVFNFPPNG THSWEYWGAQ LNAMKGDLQS SLGAG | 89 |
| TB10.4 | MSQIMYNYPA MLGHAGDMAG YAGTLQSLGA EIAVEQAALQ SAWQGDTGIT YQAWQAQWNQ AMEDLVRAYH AMSSTHEANT MAMMARDTAE AAKWGG | 90 |
| ORF2c | MIVGAAGGMP PMAPLAPLLP AAADIGLHII VTCQMSQAYK ATMDKFVGAA FGSGAPTMFL SGEKQEFPSS EFKVKRRPPG QAFLVSPDGK VIQAPYIEPP EEVFAAPPSA G | 91 |
| Rv1036 | LIPGRMVLNW EDGLNALVAE GIEAIVFRTL GDQCWLWESL LPDEVRRLPE ELARVDALLD DPAFFAPFVP FFDPRRGRPS TPMEVYLQLM FVKFRYRLGY ESLCREVADS IT | 92 |
| Rv0285 | MTLRVVPEGL AAASAAVEAL TARLAAAHAS AAPVITAVVP PAADPVSLQT AAGFSAQGVE HAVVTAEGVE ELGRAGVGVG ESGASYLAGD AAAAATYGVV GG | 93 |
| Rv0287 | MSLLDAHIPQ LVASQSAFAA KAGLMRHTIG QAEQAAMSAQ AFHQGESSAA FQAAHARFVA AAAKVNTLLD VAQANLGEAA GTYVAADAAA ASTYTGF | 94 |

Preferred combinations of fusion polypeptides comprise the following polypeptides in various combinations in order of units with one or more starvation induced antigens (X): ESAT6-Ag85A-X, ESAT6-Ag85B-X, Ag8A-X, Ag85B-X, TB10-Ag85A-X, TB10-Ag85B-X where X is any of the starvation induced antigens and where the order of the units of antigens can be of any combination e.g. where the order is reversed or X is positioned in the middle etc.

But the fusion polypeptide could be constructed from any other combination of one or more starvation induced antigen with one or more *M. tuberculosis* antigen.

Within the scope of the present invention is an analogue of a fusion polypeptide which has an amino acid sequence with a sequence identity of at least 80% to any part of any one of the fusion polypeptides of the invention and which is immunogenic, and a nucleic acid sequence which encodes such polypeptide. Such analogues are comprised within the term "polypeptide of the invention" or "fusion polypeptide of the invention" which terms are used interchangeably throughout the specification and claims. By the term "nucleic acid sequence of the invention" is meant a nucleic acid sequence encoding such a polypeptide. Further within the scope of the present invention are short or long peptide(s) overlapping or non-overlapping which has an amino acid sequence with a sequence identity of at least 80% to any one of the fusion polypeptides of the invention and which is immunogenic A presently preferred embodiment of the invention is a vaccine to boost immunity from prior BCG vaccination, i.e. the vaccine is administered to individuals previously vaccinated with BCG.

This first aspect of the invention comprises a variant of the above mentioned starvation induced antigen or fusion polypeptide which is lipidated so as to allow a self-adjuvating effect of the polypeptide.

The immunogenic composition, vaccine or pharmaceutical composition of the invention can be administered by mucosal delivery, e.g. orally, nasally, buccally, or traditionally intramuscularly, intradermally, by subcutaneous injection or transdermally or any other suitable route, e.g. rectally.

In another embodiment, the invention discloses the use of a starvation induced antigen or a fusion polypeptide as defined above for the preparation of an immunogenic composition, vaccine or pharmaceutical composition which can be used for a prophylactic vaccination together with BCG, a booster vaccine or therapeutical vaccination against an infection caused by a virulent *mycobacterium*, e.g. by *Mycobacterium tuberculosis*, *Mycobacterium africanum*, *Mycobacterium Bovis*, *Mycobacterium leprae* or *Mycobacterium ulcerans*.

In a second aspect, the invention discloses an immunogenic composition, vaccine or pharmaceutical composition which comprises a nucleotide sequence which encodes a starvation induced antigen or a fusion polypeptide as defined above, or comprises a nucleic acid sequence complementary thereto which is capable of hybridizing to the nucleic acid sequence of the invention under stringent conditions.

The nucleic acid fragment is preferably a DNA fragment. The fragment can be used as a pharmaceutical as discussed in the following.

In one embodiment, the invention discloses an immunogenic composition, vaccine or pharmaceutical composition comprising a nucleic acid fragment according to the invention, optionally inserted in a vector. The vaccine resulting in vivo expression of antigen by an animal, including a human being, to whom the vaccine has been administered, the amount of expressed antigen being effective to confer substantially increased resistance to *tuberculosis* caused by virulent mycobacteria, e.g. by *Mycobacterium tuberculosis, Mycobacterium africanum, Mycobacterium bovis, Mycobacterium leprae* or *Mycobacterium ulcerans*, in an animal, including a human being.

In a further embodiment, the invention discloses the use of an immunogenic composition, vaccine or pharmaceutical composition comprising a nucleic acid fragment according to the invention for therapeutic vaccination against *tuberculosis* caused by a virulent *mycobacterium*.

In a still further embodiment, the invention discloses an immunogenic composition, vaccine or pharmaceutical composition which can be used for prophylactic vaccination together with BCG or as a booster vaccine to a person previously vaccinated with BCG for immunizing an animal, including a human being, against *tuberculosis* caused by a virulent *mycobacterium*, e.g. by *Mycobacterium tuberculosis, Mycobacterium africanum, Mycobacterium bovis, Mycobacterium leprae* or *Mycobacterium ulcerans*, comprising as the effective component a non-pathogenic microorganism, such as vaccinia, adenovirus or *Mycobacterium bovis* BCG, wherein at least one copy of a DNA fragment comprising a DNA sequence encoding a fusion polypeptide as defined above has been incorporated into the microorganism (e.g. placed on a plasmid or in the genome) in a manner allowing the microorganism to express and optionally secrete the fusion polypeptide.

In another embodiment, the invention discloses an infectious expression vector, such as vaccinia, adenovirus or *Mycobacterium bovis* BCG which comprises a nucleic acid fragment according to the invention, and a transformed cell harboring at least one such vector.

In a third aspect, the invention discloses a method for immunizing and boosting the immunity of an animal, including a human being, against *tuberculosis* caused by virulent mycobacteria, e.g. by *Mycobacterium tuberculosis, Mycobacterium africanum, Mycobacterium bovis, Mycobacterium leprae* or *Mycobacterium ulcerans*, the method comprising administering to the animal the fusion polypeptide as defined above, the immunogenic composition according to the invention, or the vaccine according to the invention.

In a fourth aspect, the invention discloses a method for treating an animal, including a human being, having *tuberculosis*, active or latent, caused by virulent mycobacteria, e.g. by *Mycobacterium tuberculosis, Mycobacterium africanum, Mycobacterium bovis, Mycobacterium leprae* or *Mycobacterium ulcerans*, the method comprising administering to the animal the immunogenic composition, vaccine or pharmaceutical composition as defined above.

In a fifth aspect, the invention discloses the use of a starvation induced antigen or a fusion polypeptide or nucleic acid fragment as defined above for the preparation of an immunogenic composition, vaccine or pharmaceutical composition in combination with *M. bovis* BCG, e.g. for a prophylactic (including boosting) or therapeutical vaccination against an infection caused by a virulent *mycobacterium*, e.g. by *Mycobacterium tuberculosis, Mycobacterium africanum, Mycobacterium bovis, Mycobacterium leprae* or *Mycobacterium ulcerans*.

The vaccine, immunogenic composition, vaccine and pharmaceutical composition according to the invention can be used prophylactically in a subject not infected with a virulent *mycobacterium* or in an individual previously vaccinated with *M. tuberculosis* BCG or therapeutically in a subject infected with a virulent *mycobacterium*.

It is to be understood that the embodiments of the first aspect of the invention, such as the immunogenic polypeptides described also apply to all other aspects of the invention; and vice versa.

Throughout this specification, unless the context requires otherwise, the word "comprise", or variations thereof such as "comprises" or "comprising", will be understood to imply the inclusion of a stated element or integer or group of elements or integers but not the exclusion of any other element or integer or group of elements or integers.

DEFINITIONS

Starvation

By the term "starvation" is understood depriving an organism of its carbon, nitrogen or energy source, any combination of the above or even all of them.

Starvation Induced Proteins

By the term "starvation induced proteins" is understood any protein that at the transcriptional or protein level is induced (increased) at least 6.5 fold after stressing the mycobacteria by starvation.

Combination with *M. bovis* BCG

By the term "combination with *M. bovis* BCG" is understood co-administration with any *M. bovis* BCG strain including, Pasteur, Phipps, Frappier, Connaught, Tice, Denmark, Glaxo, Prague, Birkhaug, Sweden, Japan, Moreau and Russia in quantities that lead either to a significant increased specific immune response or to a significant protection in an animal model or a human either together with one or more of the fusion polypeptides defined above or with one or more of the nucleic acid fragments encoding these, or administered at the same time but at separate sites or routes.

Boost of *M. bovis* BCG

By the term "boost of *M. bovis* BCG" is understood administration of one or more fusion polypeptides as defined above or one or more nucleic acid fragments encoding these at any period after vaccination with any *M. bovis* BCG strain including, Pasteur, Phipps, Frappier, Connaught, Tice, Denmark, Glaxo, Prague, Birkhaug, Sweden, Japan, Moreau and Russia in quantities that lead either to a significantly increased specific immune response or a significantly increased protection in an animal model or a human.

Polypeptide

A preferred polypeptide to be used as a unit of the fusion polypeptides of the present invention is an immunogenic polypeptide from *M. tuberculosis*. Such polypeptide can for example be based on a polypeptide derived from the *M. tuberculosis* cell and/or *M. tuberculosis* culture filtrate. The polypeptide will normally be a recombinant or synthetic polypeptide and may consist of the immunogenic polypeptide, an immunogenic portion thereof or may contain additional sequences. The additional sequences may be derived from the native M. tuberculosis antigen or be heterologous and such sequences may, but need not, be immunogenic.

By the term "fusion polypeptide" is understood a random order of two or more immunogenic polypeptides from M. tuberculosis or analogues thereof fused together with or without an amino acid spacer(s) of arbitrary length and sequence.

The word "polypeptide" in the present invention should have its usual meaning. That is an amino acid chain of any length, including a full-length protein, oligopeptide, short peptide and fragment thereof and fusion polypeptide, wherein the amino acid residues are linked by covalent peptide bonds.

The polypeptide may be chemically modified by being glycosylated, by being lipidated (e.g. by chemical lipidation with palmitoyloxy succinimide as described by Mowat et al. 1991 or with dodecanoyl chloride as described by Lustig et al. 1976), by comprising prosthetic groups, or by containing additional amino acids such as e.g. a his-tag or a signal peptide.

Each immunogenic polypeptide will be characterized by specific amino acids and be encoded by specific nucleic acid sequences. Within the scope of the present invention are such sequence and analogues and variants produced by recombinant or synthetic methods wherein such polypeptide sequences have been modified by substitution, insertion, addition or deletion of one or more amino acid residues in the recombinant polypeptide while still being immunogenic in any of the biological assays described herein.

Substitutions are preferably "conservative". These are defined according to the following table. Amino acids in the same block in the second column and preferably in the same line in the third column may be substituted for each other. The amino acids in the third column are indicated in one-letter code.

| ALIPHATIC | Non-polar | GAP |
| --- | --- | --- |
| | | ILV |
| | Polar-uncharged | CSTM |
| | | NQ |
| | Polar-charged | DE |
| | | KR |
| AROMATIC | | HFWY |

Each polypeptide is encoded by a specific nucleic acid sequence. Within the scope of the present invention are analogues and such nucleic acid sequences which have been modified by substitution, insertion, addition or deletion of one or more nucleic acids. Substitutions are preferably silent substitutions in the codon usage which will not lead to any change in the amino acid sequence, but may be introduced to enhance the expression of the protein.

Nucleic Acid Fragment

By the terms "nucleic acid fragment" and "nucleic acid sequence" are understood any nucleic acid molecule including DNA, RNA, LNA (locked nucleic acids), PNA, RNA, dsRNA and RNA-DNA-hybrids. Also included are nucleic acid molecules comprising non-naturally occurring nucleosides. The term includes nucleic acid molecules of any length e.g. from 10 to 10000 nucleotides, depending on the use. When the nucleic acid molecule is for use as a pharmaceutical, e.g. in DNA therapy, or for use in a method for producing a polypeptide according to the invention, a molecule encoding at least one epitope is preferably used, having a length from about 18 to about 1000 nucleotides, the molecule being optionally inserted into a vector. When the nucleic acid molecule is used as a probe, as a primer or in antisense therapy, a molecule having a length of 10-100 is preferably used. According to the invention, other molecule lengths can be used, for instance a molecule having at least 12, 15, 21, 24, 27, 30, 33, 36, 39, 42, 50, 60, 70, 80, 90, 100, 200, 300, 400, 500 or 1000 nucleotides (or nucleotide derivatives), or a molecule having at most 10000, 5000, 4000, 3000, 2000, 1000, 700, 500, 400, 300, 200, 100, 50, 40, 30 or 20 nucleotides (or nucleotide derivatives).

The term "stringent" when used in conjunction with hybridization conditions is as defined in the art, i.e. the hybridization is performed at a temperature not more than 15-20° C. under the melting point Tm, cf. Sambrook et al, 1989, pages 11.45-11.49. Preferably, the conditions are "highly stringent", i.e. 5-10° C. under the melting point Tm.

Sequence Identity

The term "sequence identity" indicates a quantitative measure of the degree of homology between two amino acid sequences of substantially equal length or between two nucleic acid sequences of substantially equal length. The two sequences to be compared must be aligned to best possible fit possible with the insertion of gaps or alternatively, truncation at the ends of the protein sequences. The sequence identity can be calculated as $$\frac{(N_{ref} - N_{dif})100}{N_{ref}},$$

wherein $N_{dif}$ is the total number of non-identical residues in the two sequences when aligned and wherein $N_{ref}$ is the number of residues in one of the sequences. Hence, the DNA sequence AGTCAGTC (SEQ ID NO: 95) will have a sequence identity of 75% with the sequence AATCAATC (SEQ ID NO: 96) ($N_{dif}=2$ and $N_{ref}=8$). A gap is counted as non-identity of the specific residue(s), i.e. the DNA sequence AGTGTC (SEQ ID NO: 97) will have a sequence identity of 75% with the DNA sequence AGTCAGTC (SEQ ID NO: 95) ($N_{dif}=2$ and $N_{ref}=8$). Sequence identity can alternatively be calculated by the BLAST program e.g. the BLASTP program (Pearson W. R and D. J. Lipman (1988)). In one embodiment of the invention, alignment is performed with the sequence alignment method ClustalW with default parameters as described by Thompson J., et al 1994.

A preferred minimum percentage of sequence identity is at least 80%, such as at least 85%, at least 90%, at least 91%, at least 92%, at least 93%, at least 94%, at least 95%, at least 96%, at least 97%, at least 98%, at least 99%, and at least 99.5%. Preferably, the numbers of substitutions, insertions, additions or deletions of one or more amino acid residues in the fusion polypeptide is limited, i.e. no more than 1, 2, 3, 4, 5, 6, 7, 8, 9, 10 substitutions, no more than 1, 2, 3, 4, 5, 6, 7, 8, 9, 10 insertions, no more than 1, 2, 3, 4, 5, 6, 7, 8, 9, 10 additions, and no more than 1, 2, 3, 4, 5, 6, 7, 8, 9, 10 deletions compared to the immunogenic polypeptide units based on polypeptides derived from M. tuberculosis.

Immunogenic Portion

The polypeptide of the invention comprises an immunogenic portion, such as an epitope for a B-cell or T-cell.

The immunogenic portion of an immunogenic polypeptide is the part of the polypeptide, which elicits an immune response in an animal or a human being, and/or in a biological sample determined by any of the biological assays described herein. The immunogenic portion of a polypeptide may be a T-cell epitope or a B-cell epitope. Immunogenic portions can be related to one or a few relatively small parts of the polypeptide, they can be scattered throughout the polypeptide sequence or be situated in specific parts of the polypeptide. For a few polypeptides epitopes have even been demonstrated to be scattered throughout the polypeptide covering the full sequence (Ravn et al 1999).

In order to identify relevant T-cell epitopes which are recognized during an immune response, it is possible to use a "brute force" method: Since T-cell epitopes are linear, deletion mutants of the polypeptide will, if constructed systematically, reveal what regions of the polypeptide are essential in immune recognition, e.g. by subjecting these deletion mutants e.g. to the IFN-gamma assay described herein. Another method utilizes overlapping oligopeptides for the detection of MHC class II epitopes, preferably synthetic, having a length of e.g. 20 amino acid residues derived from the polypeptide. These peptides can be tested in biological assays (e.g. the IFN-gamma assay as described herein) and some of these will give a positive response (and thereby be immunogenic) as evidence for the presence of a T cell epitope in the peptide. For the detection of MHC class I epitopes it is possible to predict peptides that will bind (Stryhn et al. 1996) and hereafter produce these peptides synthetically and test them in relevant biological assays e.g. the IFN-gamma assay as described herein. The peptides preferably having a length of e.g. 8 to 11 amino acid residues derived from the polypeptide. B-cell epitopes can be determined by analyzing the B cell recognition to overlapping peptides covering the polypeptide of interest as e.g. described in Harboe et al 1998.

Immunogenic portions of polypeptides may be recognized by a broad part (high frequency) or by a minor part (low frequency) of the genetically heterogenic human population. In addition some immunogenic portions induce high immunological responses (dominant), whereas others induce lower, but still significant, responses (subdominant). High frequency or low frequency can be related to the immunogenic portion binding to widely distributed MHC molecules (HLA type) or even by multiple MHC molecules (Kilgus et al. 1991, Sinigaglia et al 1988).

Analogues

A common feature of the fusion polypeptides of the invention is their capability to induce an immunological response as illustrated in the examples. It is understood that within the scope of the present invention are analogues of a fusion polypeptide of the invention produced by substitution, insertion, addition or deletion is also immunogenic determined by any of the assays described herein.

Substantially Pure

In the present context the term "substantially pure polypeptide" means a polypeptide preparation which contains at most 5% by weight of other polypeptide material with which it is associated natively or during recombinant or synthetic production (lower percentages of other polypeptide material are preferred, e.g. at most 4%, at most 3%, at most 2%, at most 1%, and at most ½%). It is preferred that the substantially pure polypeptide is at least 96% pure, i.e. that the polypeptide constitutes at least 96% by weight of total polypeptide material present in the preparation, and higher percentages are preferred, such as at least 97%, at least 98%, at least 99%, at least 99.25%, at least 99.5%, and at least 99.75%. It is especially preferred that the polypeptide is in "essentially pure form", i.e. that the polypeptide is essentially free of any other antigen with which it is natively associated, i.e. free of any other antigen from bacteria belonging to the *tuberculosis* complex or a virulent *mycobacterium*. This can be accomplished by preparing the polypeptide by means of recombinant methods in a non-mycobacterial host cell as will be described in detail below, or by synthesizing the polypeptide by the well-known methods of solid or liquid phase peptide synthesis, e.g. by the method described by Merrifield or variations thereof, and by using appropriate purification procedures well known to the person of ordinary skill in the art (Merrifield 1962, Merrifield 1963).

Virulent *mycobacterium*, individual currently infected and immune individual

By the term "virulent *mycobacterium*" is understood a bacterium capable of causing the *tuberculosis* disease in an animal or in a human being. Examples of virulent mycobacteria are *Mycobacterium tuberculosis, Mycobacterium africanum, Mycobacterium bovis, Mycobacterium leprae* or *Mycobacterium ulcerans*. Examples of relevant animals are cattle, possums, badgers, buffaloes, lions, kurus and kangaroos.

By "an animal or human currently infected with a virulent mycobacterium" is understood an individual with culture or microscopically proven infection with virulent mycobacteria, and/or an individual clinically diagnosed with TB and who is responsive to anti-TB chemotherapy. Culture, microscopy and clinical diagnosis of TB are well known by any person skilled in the art.

An immune individual is defined as a person or an animal, which has cleared or controlled an infection with a virulent mycobacterium or has received a vaccination with *M. bovis* BCG.

Immunogenic

An immunogenic polypeptide is defined as a polypeptide that induces an immune response. The immune response may be monitored by one of the following methods:

An in vitro cellular response is determined by release of a relevant cytokine such as IFN-gamma, from lymphocytes withdrawn from an animal or human currently or previously infected with virulent mycobacteria, or by detection of proliferation of these T cells. The induction is performed by addition of the polypeptide or the immunogenic portion to a suspension comprising from $1\times10^5$ cells to $3\times10^5$ cells per well. The cells are isolated from either blood, the spleen, the liver or the lung and the addition of the polypeptide or the immunogenic portion of the polypeptide result in a concentration of not more than 20 ug per ml suspension and the stimulation is performed from two to five days. For monitoring cell proliferation the cells are pulsed with radioactive labeled thymidine and after 16-22 hours of incubation the proliferation is detected by liquid scintillation counting. A positive response is a response more than background plus two standard deviations. The release of IFN-gamma can be determined by the ELISA method, which is well known to a person skilled in the art. A positive response is a response more than background plus two standard deviations. Other cytokines than IFN-gamma could be relevant when monitoring an immunological response to the polypeptide, such as IL-12, TNF-α, IL-4, IL-5, IL-10, IL-6, TGF-β. Another and more sensitive method for determining the presence of a cytokine (e.g. IFN-gamma) is the ELISPOT method where the cells isolated from either the blood, the spleen, the liver or the lung are diluted to a concentration of preferable of 1 to $4\times10^6$ cells/ml and incubated for 18-22 hrs in the presence of the polypeptide or the immunogenic portion of the polypeptide resulting in a concentration of not more than 20 ug per ml. The cell suspensions are hereafter diluted to 1 to $2\times10^6$/ml and transferred to Maxisorp plates coated with anti-IFN-gamma and incubated for preferably 4 to 16 hours. The IFN-gamma producing cells are determined by the use of labelled secondary anti-IFN-antibody and a relevant substrate giving rise to spots, which can be enumerated using a dissection microscope. It is also a possibility to determine the presence of mRNA coding for the relevant cytokine by the use of the PCR technique. Usually one or more cytokines will be measured utilizing for example the PCR, ELISPOT or ELISA. It will be appreciated by a person skilled in the art that a significant increase or decrease in the amount of any of these cytokines induced by a specific polypeptide can be used in evaluation of the immunological activity of the polypeptide.

An in vitro cellular response may also be determined by the use of T cell lines derived from an immune individual or an *M. tuberculosis* infected person where the T cell lines have been driven with either live mycobacteria, extracts from the bacterial cell or culture filtrate for 10 to 20 days with the addition of IL-2. The induction is performed by addition of not more than 20 ug polypeptide per ml suspension to the T cell lines containing from $1\times10^5$ cells to $3\times10^5$ cells per well and incubation is performed from two to six days. The induction of IFN-gamma or release of another relevant cytokine is detected by ELISA. The stimulation of T cells can also be monitored by detecting cell proliferation using radioactively labeled Thymidine as described above. For both assays a positive response is a response more than background plus two standard deviations.

An in vivo cellular response may be determined as a positive DTH response after intradermal injection or local application patch of at most 100 ug of the polypeptide or the immunogenic portion to an individual who is clinically or subclinically infected with a virulent Mycobacterium, a positive response having a diameter of at least 5 mm 72-96 hours after the injection or application.

An in vitro humoral response is determined by a specific antibody response in an immune or infected individual. The presence of antibodies may be determined by an ELISA technique or a Western blot where the polypeptide or the immunogenic portion is absorbed to either a nitrocellulose membrane or a polystyrene surface. The serum is preferably diluted in PBS from 1:10 to 1:100 and added to the absorbed polypeptide and the incubation being performed from 1 to 12 hours. By the use of labeled secondary antibodies the presence of specific antibodies can be determined by measuring the presence or absence of a specific label e.g. by ELISA where a positive response is a response of more than background plus two standard deviations or alternatively a visual response in a Western blot.

Another relevant parameter is measurement of the protection in animal models induced after vaccination with the polypeptide in an adjuvant or after DNA vaccination. Suitable animal models include primates, guinea pigs or mice, which are challenged with an infection of a virulent Mycobacterium. Readout for induced protection could be decrease of the bacterial load in target organs compared to non-vaccinated animals, prolonged survival times compared to non-vaccinated animals and diminished weight loss or pathology compared to non-vaccinated animals.

Preparation Methods

In general the fusion polypeptides of the invention, and DNA sequences encoding such fusion polypeptides, may be prepared by use of any one of a variety of procedures.

The fusion polypeptide may be produced recombinantly using a DNA sequence encoding the polypeptide, which has been inserted into an expression vector and expressed in an appropriate host. Examples of host cells are *E. coli*. The fusion polypeptides can also be produced synthetically having fewer than about 100 amino acids, and generally fewer than 50 amino acids and may be generated using techniques well known to those ordinarily skilled in the art, such as commercially available solid-phase techniques where amino acids are sequentially added to a growing amino acid chain.

The fusion polypeptides may also be produced with an additional fusion partner, by which methods superior characteristics of the polypeptide of the invention can be achieved. For instance, fusion partners that facilitate export of the polypeptide when produced recombinantly, fusion partners that facilitate purification of the polypeptide, and fusion partners which enhance the immunogenicity of the polypeptide of the invention are all interesting. The invention in particular pertains to a fusion polypeptide comprising fusions of two or more immunogenic polypeptides based on polypeptides derived from *M. tuberculosis*.

Other fusion partners, which could enhance the immunogenicity of the product, are lymphokines such as IFN-gamma, IL-2 and IL-12. In order to facilitate expression and/or purification, the fusion partner can e.g. be a bacterial fimbrial protein, e.g. the pilus components pilin and papA; protein A; the ZZ-peptide (ZZ-fusions are marketed by Pharmacia in Sweden); the maltose binding protein; gluthatione S-transferase; β-galactosidase; or poly-histidine. Fusion proteins can be produced recombinantly in a host cell, which could be *E. coli*, and it is a possibility to induce a linker region between the different fusion partners. The linker region between e.g. the individual immunogenic polypeptide units may comprise 1, 2, 3, 4, 5, 6, 7, 8, 9 or 10 amino acids.

Interesting fusion polypeptides are polypeptides of the invention, which are lipidated so that the immunogenic polypeptide is presented in a suitable manner to the immune system. This effect is e.g. known from vaccines based on the *Borrelia burgdorferi* OspA polypeptide as described in e.g. WO 96/40718 A or vaccines based on the *Pseudomonas aeruginosa* OprI lipoprotein (Cote-Sierra J 1998). Another possibility is N-terminal fusion of a known signal sequence and an N-terminal cysteine to the immunogenic polypeptide. Such a fusion results in lipidation of the immunogenic fusion polypeptide at the N-terminal cysteine, when produced in a suitable production host.

Vaccine

An important aspect of the invention pertains to a vaccine composition comprising a fusion polypeptide according to the invention. In order to ensure optimum performance of such a vaccine composition it is preferred that it comprises an immunologically and pharmaceutically acceptable carrier, vehicle or adjuvant.

An effective vaccine, wherein a fusion polypeptide of the invention is recognized by the animal, will in an animal model be able to decrease bacterial load in target organs, prolong survival times and/or diminish weight loss or pathology after challenge with a virulent *Mycobacterium*, compared to non-vaccinated animals.

Suitable carriers are selected from the group consisting of a polymer to which the polypeptide(s) is/are bound by hydrophobic non-covalent interaction, such as a plastic, e.g. polystyrene, or a polymer to which the polypeptide(s) is/are covalently bound, such as a polysaccharide, or a polypeptide, e.g. bovine serum albumin, ovalbumin or keyhole limpet haemocyanin. Suitable vehicles are selected from the group consisting of a diluent and a suspending agent. The adjuvant is preferably selected from the group consisting of dimethyloctadecylammonium bromide (DDA), dimethyloctadecenylammonium bromide (DODAC), QuilA, poly I:C, aluminium hydroxide, Freund's incomplete adjuvant, IFN-gamma, IL-2, IL-12, monophosphoryl lipid A (MPL), Trehalose Dimycolate (TDM), Trehalose Dibehenate and muramyl dipeptide (MDP) or mycobacterial lipid extract, in particular apolar lipid extracts as disclosed in PCT/DK2004/000488.

Preparation of vaccines which contain polypeptides as active ingredients is generally well understood in the art, as exemplified by U.S. Pat. Nos. 4,608,251; 4,601,903; 4,599, 231 and 4,599,230, all incorporated herein by reference.

Other methods of achieving adjuvant effect for the vaccine include use of agents such as aluminum hydroxide or phosphate (alum), synthetic polymers of sugars (Carbopol), aggregation of the protein in the vaccine by heat treatment, aggregation by reactivating with pepsin treated (Fab) antibodies to albumin, mixture with bacterial cells such as *C. parvum* or endotoxins or lipopolysaccharide components of gram-negative bacteria, emulsion in physiologically acceptable oil vehicles such as mannide mono-oleate (Aracel A) or emulsion with 20 percent solution of a perfluorocarbon (Fluosol-DA) used as a block substitute may also be employed. Other possibilities involve the use of immune modulating substances such as cytokines or synthetic IFN-gamma inducers such as poly I:C in combination with the above-mentioned adjuvants.

Another interesting possibility for achieving adjuvant effect is to employ the technique described in Gosselin et al., 1992 (which is hereby incorporated by reference herein). In brief, a relevant antigen such as an antigen of the present invention can be conjugated to an antibody (or antigen binding antibody fragment) against the Fc-receptors on monocytes/macrophages.

To improve the BCG vaccine, one or more relevant antigen(s) such as one or more fusion polypeptides of the present invention can be mixed with a BCG vaccine before administration and injected together with the BCG vaccine thereby obtaining a synergistic effect leading to a better protection. Another interesting possibility for achieving a synergistic effect is to keep the BCG vaccine and the fusion polypeptide(s) of the present invention separate but use them at the same time and administer them at different sites or through different routes.

To boost the currently used BCG vaccines a relevant antigen such as one or more of the fusion polypeptides of the present invention can be administrated at the time where the BCG vaccines typically start waning or even before, such as 2, 5, 10, 15, 20, 25, 30, 35, 40, 50, 55, 60, 65 or 70 years after BCG vaccination. It could thereafter be given at regular intervals, such as 1, 2, 3, 4, 5 or 10 years, for up to 5 times.

The vaccines are administered in a manner compatible with the dosage formulation, and in such amount as will be prophylactic or therapeutically effective and immunogenic. The quantity to be administered depends on the subject to be treated, including, e.g., the capacity of the individual's immune system to mount an immune response, and the degree of protection desired. Suitable dosage ranges are of the order of several hundred micrograms of the fusion polypeptide of the invention per vaccination with a preferred range from about 0.1 μg to 1000 μg, such as in the range from about 1 μg to 300 μg, and especially in the range from about 10 μg to 100 μg. Suitable regimens for initial administration and booster shots are also variable but are typified by an initial administration followed by subsequent inoculations or other administrations.

The manner of application may be varied widely. Any of the conventional methods for administration of a vaccine are applicable. These include oral, nasal or mucosal application in either a solid form containing the active ingredients (such as a pill, suppository or capsule) or in a physiologically acceptable dispersion, such as a spray, powder or liquid, or parenterally, by injection, for example, subcutaneously, intradermally or intramuscularly or transdermally applied. The dosage of the vaccine will depend on the route of administration and will vary according to the age of the person to be vaccinated and, to a lesser degree, the size of the person to be vaccinated. Currently, most vaccines are administered intramuscularly by needle injection and this is likely to continue as the standard route. However, vaccine formulations which induce mucosal immunity have been developed, typically by oral or nasal delivery. One of the most widely studies delivery systems for induction of mucosal immunity contains cholera toxin (CT) or its B subunit. This protein enhances mucosal immune responses and induces IgA production when administered in vaccine formulations. An advantage is the ease of delivery of oral or nasal vaccines. Modified toxins from other microbial species, which have reduced toxicity but retained immunostimulatory capacity, such as modified heat-labile toxin from Gram-negative bacteria or staphylococcal enterotoxins may also be used to generate a similar effect. These molecules are particularly suited to mucosal administration.

The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides; such suppositories may be formed from mixtures containing the active ingredient in the range of 0.5% to 10%, preferably 1-2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and advantageously contain 10-95% of active ingredient, preferably 25-70%.

In many instances, it will be necessary to have multiple administrations of the vaccine. Especially, vaccines can be administered to prevent an infection with virulent mycobacteria and/or to treat established mycobacterial infection or to boost a previous BCG vaccinated person. When administered to prevent an infection, the vaccine is given prophylactically, before definitive clinical signs or symptoms of an infection are present.

Due to genetic variation, different individuals may react with immune responses of varying strength to the same polypeptide. Therefore, the vaccine according to the invention may comprise several different fusion polypeptides and/or polypeptides in order to increase the immune response. The vaccine may comprise two or more fusion polypeptides or starvation induced polypeptides or immunogenic portions hereof, where all of the starvation induced antigens or fusion polypeptides are as defined above, or some but not all of the polypeptides may be derived from virulent mycobacteria. In the latter example, the polypeptides not necessarily fulfilling the criteria set forth above for fusion polypeptides may either act due to their own immunogenicity or merely act as adjuvants.

The vaccine may comprise 1-20, such as 2-20, or even 3-20 different polypeptides or fusion polypeptides, such as 3-10 different polypeptides or fusion polypeptides.

The invention also pertains to a method for immunizing an animal, including a human being, against TB caused by virulent mycobacteria, comprising administering to the animal the fusion polypeptide of the invention, or a vaccine composition of the invention as described above, or a live vaccine described above. In a presently preferred embodiment, the animal or human is an immune individual as defined above.

The invention also pertains to a method for producing an immunogenic composition according to the invention, the method comprising preparing, synthesizing or isolating a fusion polypeptide according to the invention, and solubilizing or dispersing the fusion polypeptide in a medium for a vaccine, and optionally adding other *M. tuberculosis* antigens and/or a carrier, vehicle and/or adjuvant substance.

The nucleic acid fragments of the invention may be used for effecting in vivo expression of immunogenic polypeptides, i.e. the nucleic acid fragments may be used in so-called DNA vaccines as reviewed in Ulmer et al 1993, which is included by reference.

Figure 7:
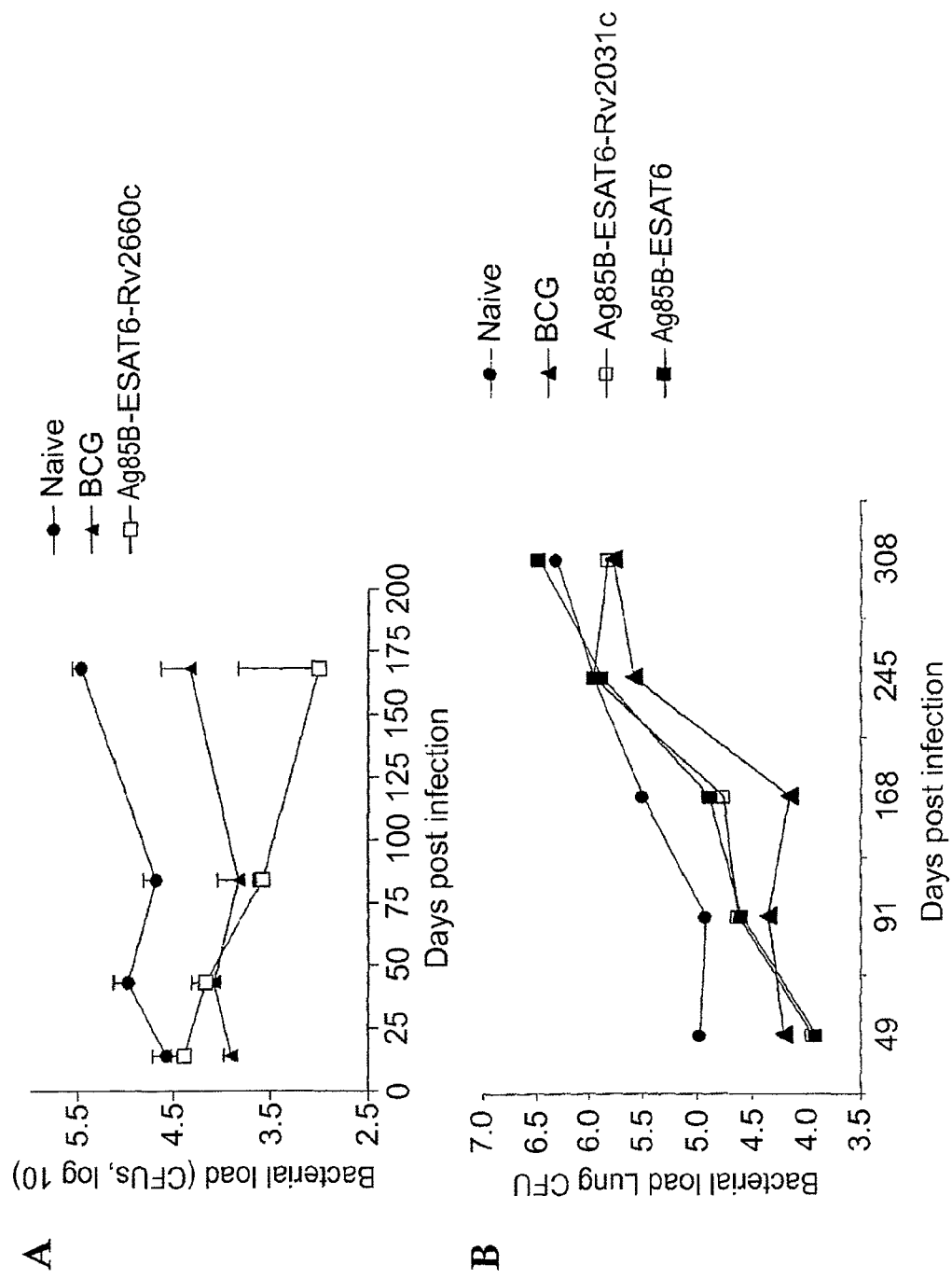

In the construction and preparation of plasmid DNA encoding a fusion polypeptide to be used defined for DNA vaccination a host strain such as *E. coli* can be used. Plasmid DNA can then be prepared from overnight cultures of the host strain carrying the plasmid of interest, and purified using e.g. the Qiagen Giga-Plasmid column kit (Qiagen, Santa Clarita, Calif., USA) including an endotoxin removal step. It is essential that plasmid DNA used for DNA vaccination is endotoxin free.

Hence, the invention also relates to a vaccine comprising a nucleic acid fragment according to the invention, the vaccine effecting in vivo expression of the immunogenic polypeptide by an animal, including a human being, to whom the vaccine has been administered, the amount of expressed polypeptide being effective to confer substantially increased resistance to infections caused by virulent mycobacteria in an animal, including a human being.

The efficacy of such a DNA vaccine can possibly be enhanced by administering the gene encoding the expression product together with a DNA fragment encoding a polypeptide which has the capability of modulating an immune response.

One possibility for effectively activating a cellular immune response can be achieved by expressing the relevant immunogenic polypeptide in a non-pathogenic microorganism or virus. Well-known examples of such microorganisms are *Mycobacterium Bovis* BCG, *Salmonella* and *Pseudomona* and examples of viruses are Vaccinia Virus and Adenovirus.

Therefore, another important aspect of the present invention is an improvement of the live BCG vaccine presently available, wherein one or more copies of a DNA sequence encoding one or more fusion polypeptides as defined above has been incorporated into the genome of the micro-organism in a manner allowing the micro-organism to express and secrete the fusion polypeptide. The incorporation of more than one copy of a nucleic acid sequence of the invention is contemplated to enhance the immune response.

Another possibility is to integrate the DNA encoding the fusion polypeptide according to the invention in an attenuated virus such as the vaccinia virus or Adenovirus (Rolph et al 1997). The recombinant vaccinia virus is able to enter within the cytoplasma or nucleus of the infected host cell and the fusion polypeptide of interest can therefore induce an immune response, which is envisioned to induce protection against TB.

The invention also relates to the use of a fusion polypeptide or nucleic acid of the invention for use as therapeutic vaccines as have been described in the literature exemplified by D. Lowry (Lowry et al 1999). Antigens with therapeutic properties may be identified based on their ability to diminish the severity of *M. tuberculosis* infection in experimental animals or prevent reactivation of previous infection, when administered as a vaccine. The composition used for therapeutic vaccines can be prepared as described above for vaccines.

FIGURE LEGENDS

FIG. 1:

Antibody responses to Rv2660c for HIV-negative (TB+/HIV−) and HIV-positive (TB+/HIV+) TB patients from Uganda and healthy controls from Denmark (Controls). The cut-off was based on ROC-curve analysis with a specificity level of 97%. The observed sensitivity is shown above the graphical presentation of the data.

FIG. 2: Immunogenicity of Rv2659c

Groups of F1(Balb/cxC57BL/6) mice were subcutaneously vaccinated three times at two-week intervals with Rv2659c in DDA/MPL. One week after the final vaccination, PBMCs were analyzed by ELISA for IFN-gamma secretion following stimulation with 5 microgram/ml Rv2659c.

FIG. 3: Rv2659c induce protection against infection with *M. tuberculosis*

Groups of Balb/c-057BL/6 mice were subcutaneously vaccinated three times at two-week intervals with Rv2659c and protective efficacy was assessed by reduction in CFU counts in lungs and compared to unimmunized and BCG immunized mice 12 weeks after vaccination. Results are expressed as $\log_{10}$ colony forming units (CFU) in the lung and are mean results from 6 mice per experimental group.

FIG. 4: Immunogenicity of Rv2660c

F1(Balb/cxC57BL/6) mice were subcutaneously vaccinated three times at two-week intervals with recombinant Rv2660c protein in DDA/MPL. (A) One week after the final vaccination, PBMCs were analyzed by ELISA for IFN-gamma release following stimulation with 0.2, 1 or 5 microgram/ml of Rv2660c. Three weeks after the final vaccination, spleen cells (B) were analyzed by ELISA for IFN-gamma secretion following stimulation with 0.2, 1, or 5 microgram/ml recombinant Rv2660c and PBMCs (C) were analyzed for proliferative responses after stimulation with 0.2, 1 or 5 microgram/ml recombinant Rv2660c.

FIG. 5: Protection against infection with *Mycobacterium tuberculosis* induced by Rv2660c Groups of Balb/c-057BL/6 mice were subcutaneously vaccinated three times at two-week intervals with Rv2660c, and protective efficacy was assessed by CFU counts in lungs and compared to unimmunized and BCG immunized mice 6 weeks after aerosol infection. Results are expressed as $\log_{10}$ colony forming units (CFU) in the lung and are mean results from 6 mice per experimental group. As a positive control, a single dose of BCG Danish 1331 ($5\times10^4$ bacilli/mouse) was injected s.c. at the base of the tail at the same time as the first subunit vaccination; no booster injections were administered.

FIG. 6: Immunogenicity of Hybrid56, HyVac21 and HyVac28

Groups of F1 (Balb/cxC57BL/6) mice were subcutaneously vaccinated three times at two-week intervals with 5 microgram Ag85B-ESAT6-Rv2660c (H56), Ag85A-TB10.4-Rv2660c (H21) or Ag85B-TB10.4-Rv2660c (H28) in DDA/TDB (LipoVac). One week after the final vaccination, PBMCs were analyzed by ELISA for IFN-gamma release following stimulation with 1 microgram/ml of the fusion protein used for immunization, Ag85B, TB10.4 or Rv2660c (FIG. 6A-C).

FIG. 6D: Three weeks after the final vaccination with Ag85B-ESAT6, Ag85B-ESAT6-Rv2660c or Ag85B-ESAT6-Rv0285PBMCs were analyzed by ELISA for IFN-gamma secretion following stimulation with 1 microgram/ml of indicated antigens. FIG. 6E: Alternatively, spleen cells were analyzed for proliferative responses following stimulation with 1 microgram/ml of indicated antigens.

FIG. 7: Strong protection against *M. tuberculosis* infection after immunization with Hybrid56

(A) Groups of Balb/c-C57BL/6 mice were subcutaneously vaccinated three times at two-week intervals with Ag85B-ESAT6-Rv2660c (Hybrid56), and protective efficacy was assessed by CFU counts in lungs and compared to unimmunized and BCG immunized mice 2, 6, 12 and 24 weeks after aerosol infection. (B) Groups of B6 mice were subcutaneously vaccinated three times at two-week intervals with either Ag85B-ESAT6 (Hybrid1) or Ag85B-ESAT6-Rv2031c (Hybrid32) and protective efficacy was assessed by CFU counts in lungs and compared to unimmunized and BCG immunized mice 7, 13, 24, 35 and 44 weeks after aerosol infection Results are expressed as $\log_{10}$ colony forming units (CFU) in the lung and are mean results from 6 mice per experimental group. As a positive control, a single dose of BCG Danish 1331 ($5 \times 10^4$ bacilli/mouse) was injected s.c. at the base of the tail at the same time as the first subunit vaccination; no booster injections were administered.

Figure 8:
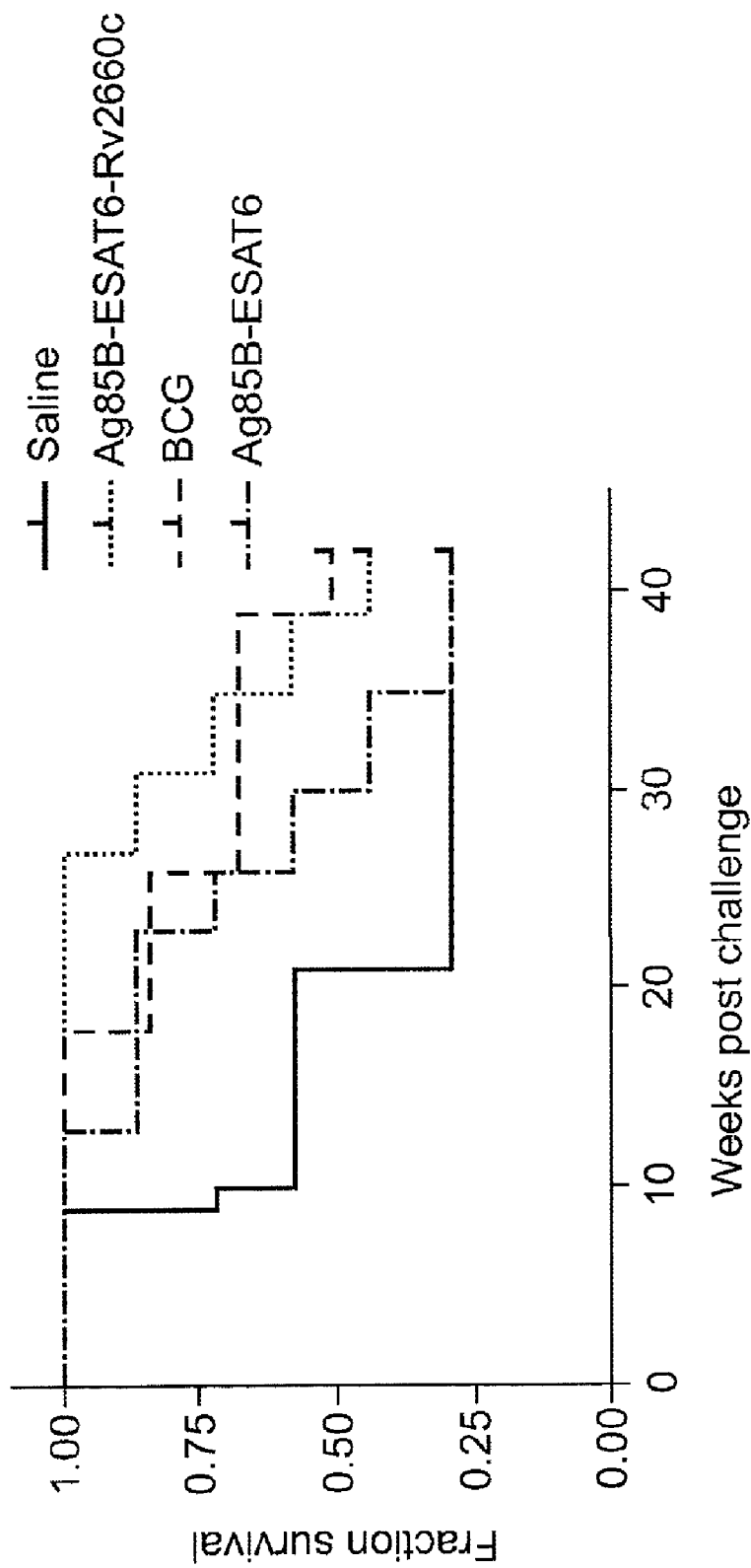

FIG. 8: Kaplan-Meier survival curves (n=7)

Immunization of guinea pigs with Ag85B-ESAT6-Rv2660c fusion protein prolongs survival time to the level of BCG immunized animals after low-dose aerosol *M. tuberculosis* challenge.

Figure 9:
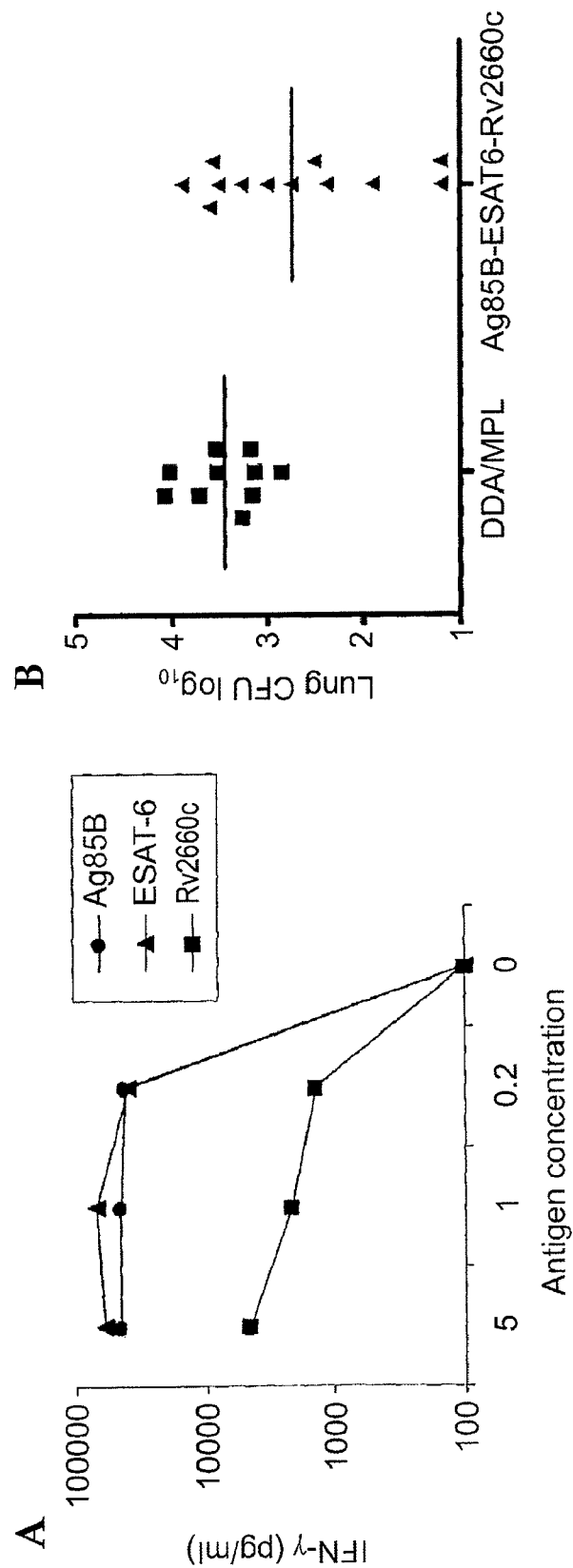

FIG. 9: Hybrid56 (Ag85b-ESAT6-Rv2660c) induced immunogenicity and protection

F1(Balb/cxC57BL/6) mice were subcutaneously vaccinated three times at two-week intervals with Ag85B-ESAT6-Rv2660c (Hybrid56) in DDA/MPL. Ten weeks after the final vaccination, spleen cells were analyzed by ELISA for IFN-gamma secretion following stimulation with 0.2, 1, or 5 ug/ml Ag85B, ESAT6, or Rv2660c (as noted in FIG. 9A). Protective efficacy was assessed by reduction in CFU counts in lungs compared to adjuvant control immunized mice ten weeks after vaccination. Results are expressed as $\log_{10}$ colony forming units (CFU) in the lung from 12 mice per experimental group (FIG. 9B).

EXAMPLES

A. Materials and Methods
B. Animals

Female specific-pathogen-free C57BL/6xBalb/C F1 or C57BL/6 mice, 8 to 16 weeks of age, obtained from Bomholtegaard, Denmark were used for analysis of immune responses and studies of protection as assessed by CFU analysis. Infection studies were performed in the BSL3 facilities at Statens Serum Institute. Animals were housed in isolator cages and fed water and sterile food ad libitum. All animals were allowed a 1-week rest period before initiation of experiments.

C. Recombinant Antigen Preparations

Recombinant Ag85B-ESAT6 (Hybrid1) was produced as previously described (Olsen, van Pinxteren et al. 2001). Briefly, the His-tagged protein was expressed in *Escherichia coli* XL-1 Blue and purified on a Talon column followed by protein anion-exchange chromatography using a HiTrap Q column (Pharmacia, Uppsala, Sweden). The sample was dialyzed against 25 mM HEPES buffer (pH 8.0)-0.15 M NaCl-10% glycerol-0.01% Tween 20 before dilution and storage.

Recombinant Rv2660c was produced by the same procedure previously described for other small mycobacterial protein (Skjot, Oettinger et al. 2000). Briefly, the full-length Rv2660c gene was PCR-amplified from *M. tuberculosis* genomic DNA and subcloned into the expression plasmid pDest17. The recombinant protein was produced in *Escherichia coli* B121 blue and purified by metal ion affinity chromatography on a Ni+ column essentially as described previously (Theisen, Vuust et al. 1995) but with phosphate buffers containing 8 M urea, which was removed after the purification.

The Hybrid56 (Ag85B-ESAT6-Rv2660c), Hybrid32 (Ag85B-ESAT6-Rv2031c), HyVac21 (Ag85A-TB10.4-Rv2660c and HyVac28 (Ag85B-TB10.4-Rv2660c) fusion proteins were cloned into expression vector pDest17 (Invitrogen) by site-specific recombination according to the manufacturer.

The fusion proteins were expressed in *E. coli* strain BL21 after induction by IPTG. All four recombinant fusion proteins were collected as inclusion bodies after disruption of the cells by mild detergent (B-PER, Sigma) and sonication. Washed inclusion bodies were dissolved in 20 mM NaOAc+8 M urea at pH 4.9 and passed over an Q sepharose column to capture endotoxin. The collected run-through was diluted in Bis-tris buffer+8 M urea pH 6.5 and the pH was adjusted to pH 6.5. The protein was then passed over a CM sepharose to capture impurities and then captured on a Q sepharose column. The column was washed with bis-tris buffer pH 6.5+3 M urea. Bound proteins were eluted with NaCl. The protein was then buffer exchanged on a Sephadex column to 25 mM tris-HCl pH 8 and 10% glycerol.

Human Recognition—Serology

All sera were depleted of cross-reactive antibodies prior to use in ELISA by addition of 20 µl of *E. coli* extract (S3761, Promega, Madison, Wis.) to 200 µl serum sample followed by incubation for 4 hours at room temperature while mixing. After centrifugation (10.000×g, 10 min), 0.05% sodium azide was added to the supernatant. The ELISA was performed as follows, 96-well Maxisorp (Nunc, Roskilde, Denmark) microtiter plates were coated over night at 4° C. with antigen at 1.0 µg/ml (100 µl per well) in carbonate-bicarbonate buffer (pH 9.6). Plates were then washed 3 times with PBS containing 0.05% Tween 20 (PBS-T). Serum samples were diluted 1:100 in PBS containing 0.2% Tween 20 and 1.0% (wt/vol) bovine serum albumin (dilution buffer), and 0.1 ml of diluted serum was added to the wells in duplicate, and incubated for one hour at room temperature. After washings 3× with PBS-T, plates were incubated for one hour with 100 ul Peroxidase conjugated rabbit-anti-human Ig (P212, DAKO, Glostrup, Denmark) diluted 1:8000 in dilution buffer. Plates were washed 3 times with PBS-T and incubated with Tetramethylbenzidine substrate (TMB plus, Kem-En-Tec, Taastrup, Denmark) for 30 minutes, and the development was stopped by addition of 1 M $H_2SO_4$. Optical density at 405 nm ($OD_{405}$) was then measured.

D. Vaccine Preparation and Immunization Procedure

Mice were immunized with 5 micro g recombinant vaccine (either Rv2659c, Rv2660c, Hybrid56, HyVac21, HyVac28 or Hybrid32) delivered in 25 µg monophosphoryl lipid A (MPL, Corixa, Wash., USA) emulsified in dioctadecylammonium bromide (DDA, 250 µg/dose, Eastman Kodak, Inc., Rochester, N.Y.) in a total volume of 200 µl, as recently described (Olsen, van Pinxteren et al. 2001). The vaccines (0.2 ml/mice) were injected three times subcutaneously (s.c.) on the back with 2-week intervals. A single dose of BCG Danish 1331 ($5 \times 10^4$ bacilli/mouse) was injected s.c. at the base of the tail at the same time as the first subunit vaccination; no booster injections were administered. The prechallenge immunity was typically evaluated with blood lymphocytes 5 and 7 weeks after the first vaccination and splenocytes 7 weeks after first vaccination.

E. Experimental Infections and Bacterial Enumeration in Organs

To evaluate the level of protection, mice were challenged 10 weeks after the first immunization either by the aerosol route in a Glas-Col inhalation exposure system, calibrated to deliver approximately 100 CFU of *M. tuberculosis* Erdman per lung. Mice were sacrificed 2, 6, 12 or 24 weeks later (Hybrid56), or 7, 13, 24, 35 or 44 weeks later (Hybrid32), and lungs and spleens were removed for bacterial enumeration. The organs were homogenized separately in sterile saline, and serial dilutions were plated onto Middlebrook 7H11 agar supplemented with 2 mg of 2-thiophene-carboxylic acid hydrazide per ml to selectively inhibit the growth of residual BCG in the test organs. Colonies were counted after 2 to 3 weeks of incubation at 37° C.

F. Lymphocyte Cultures

Organs were homogenized by maceration through a fine mesh stainless steel sieve into complete RPMI (GIBCO, Grand Island, N.Y., including 2 mM glutamine, 100 U/ml each of penicillin 6-potassium and streptomycin sulphate, 10% FCS and 50 mM 2-ME).

Blood lymphocytes were purified on a density gradient lympholyte (Cedarlane, Hornby, Ontario, Canada). Cells were pooled from five mice in each group and cultured in triplicate in round-bottomed microtiter wells (96 well; Nunc, Roskilde, Denmark) containing $2\times10^5$ cells in a volume of 200 microl of RPMI 1640 medium supplemented with $5\times10^{-5}$ M 2-mercaptoethanol, 1 mM glutamine, penicillin-streptomycin 5% (vol/vol) fetal calf serum. The mycobacterial antigens were used in concentrations ranging from 5 to 0.2 mg/ml. Cultures were incubated at 37° C. in 10% CO2 for 3 days, before the removal of 100 µl of supernatant for gamma interferon (IFN-gamma determination by enzyme-linked immunosorbent assay (ELISA) as described below.

G. Enzyme-Linked Immunosorbent Assay (ELISA) for IFN-gamma

A double sandwich ELISA method was used to quantify the levels of IFN-gamma in duplicate titrations of culture supernatants, using a commercial kit for IFN-gamma assay, in accordance with the manufacturer's instructions (Mabtech, AB. Sweden). Concentrations of IFN-gamma in the samples were calculated using a standard curve generated from recombinant IFN-gamma (Life Technologies) and results are expressed in pg/ml. The difference between the duplicate wells was consistently less than 10% of the mean.

Experimental infection and vaccine efficacy evaluation in the guinea pig model.

Outbred female Hartley guinea pigs purchased from Charles River Laboratories (North Wilmington, Mass.) was given either BCG intradermally at a dose of $10^3$ CFU once or 20 µg of either Ag85B-ESAT6 or Ag85B-ESAT6-Rv2660c emulsified in DDA/MPL three times with a rest period of 3 weeks between immunizations. Six weeks after third immunization an aerosol MTB challenge was given using a device (Glas-Col, Terre Haute, Ind.) calibrated to deliver approximately 20 bacilli into each guinea pig lung. Survival times for infected guinea pigs were determined by observing animals on a daily basis for changes in food consumption, evidence of labored breathing, and behavioral changes. In addition, animals were weighed on a weekly basis until a sustained drop in weight was observed over several days, indicating illness.

H. Example 1

Human Recognition of a Starvation Induced Antigen

Rv2660c was evaluated for human recognition in a panel of pulmonary TB patients from Uganda provided by the WHO *Tuberculosis* Specimen Bank. Both patients with negative and positive HIV infection status were included (N=94 and N=73, respectively). The control group consisted of one hundred healthy, Danish resident donors with an estimated BCG coverage >90%.

Microtiter plates were coated with 1.0 µg/ml (100 µl per well) Rv2660c protein incubated with 100× diluted serum samples and developed using peroxidase conjugated rabbit-anti-human Ig and tetramethylbenzidine as substrate (results in FIG. 1).

Conclusion

In this study, the recognition of a starvation-induced protein was tested. Based upon a cutoff determined from the control group using a sensitivity of 97% if was possible to confirm the TB infection in 45% of the HIV− cases and 61% of the HIV+ cases. Clearly indicating that the RV2660c protein is expressed and recognized by the immune system during a MTB infection.

I. Example 2

Immunogenicity and Prevention of Reactivation by Post-Exposure Administration of a Starvation Induced Antigen (Rv2659c)

Figure 2:
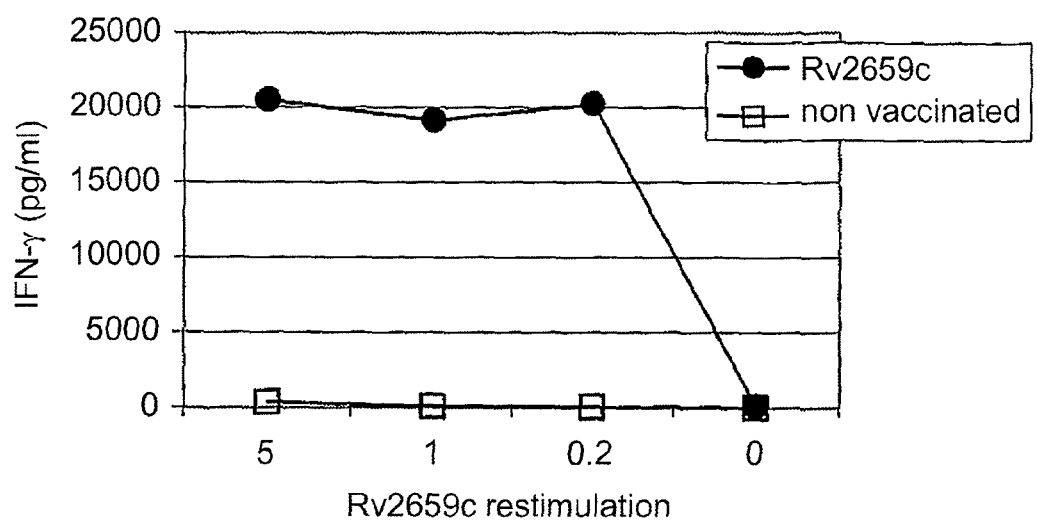

Mice were infected with *M. tuberculosis* and treated with antibiotics to reduce the bacterial burden and enter a stage of latent infection with a bacterial burden close to detection level. During the latent stage of infection the mice were vaccinated three times at two-week intervals with Rv2659c in adjuvant (e.g. DDA/MPL). One week after the final vaccination, blood cells are analyzed by ELISA for IFN-gamma secretion following stimulation with Rv2659c (FIG. 2).

The Ability of the Starvation Induced Protein Rv2659c to Induce Protection Against Reactivation of *M. tuberculosis*

Figure 3:
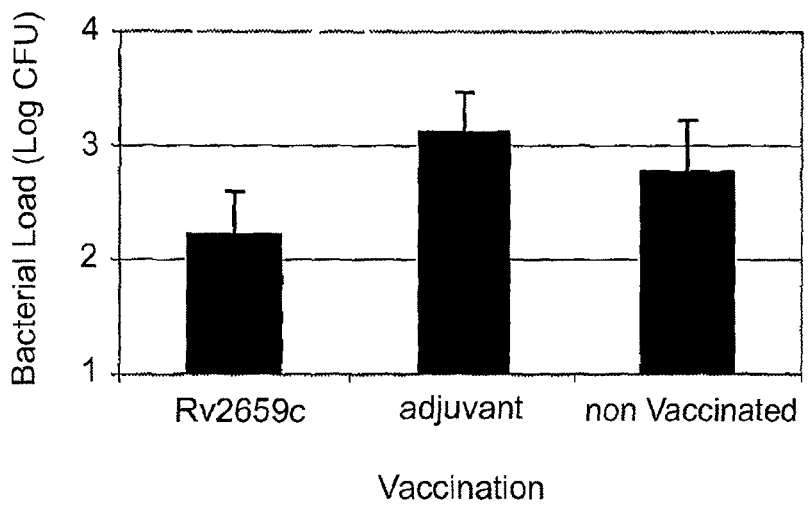

Groups of mice with latent *M. tuberculosis* were subcutaneously vaccinated three times at two-week intervals with Rv2659c formulated in adjuvant (e.g. DDA/MPL) and protective efficacy were assessed by reduction in colony forming units (CFU) from lungs and spleens when compared to non-vaccinated (latently infected) mice. Protection against reactivation was evaluated three months after vaccination. Rv2659c induced a 3 to 90 fold reduction in pulmonary bacterial levels compared to reactivated unimmunized latently infected mice (FIG. 3). To evaluate the influence of the Rv2659c vaccination on the possible development of pathology in the latently infected mice, lung tissue was taken from latently infected vaccinated mice for histopathological examination. No significant caseous necrosis, fibrosis or mineralization was detected in the lesions and no enhanced infiltration of inflammatory cells was seen.

Conclusion

In this study, the potential of a starvation induced protein, Rv2659c as a therapeutic vaccine was tested. When the Rv2659c protein was administered to mice in the adjuvant combination dimethyldioctadecylammonium bromide-monophosphoryl lipid A, a strong immune response was induced/boosted. The immunization resulted in 0.5-1.0 log reduction in the bacterial burden in the lung. Thus our studies suggest that post-exposure vaccination reduces or delays reactivation of *M. tuberculosis* without triggering pulmonary immunopathology.

J. Example 3

Figure 4:
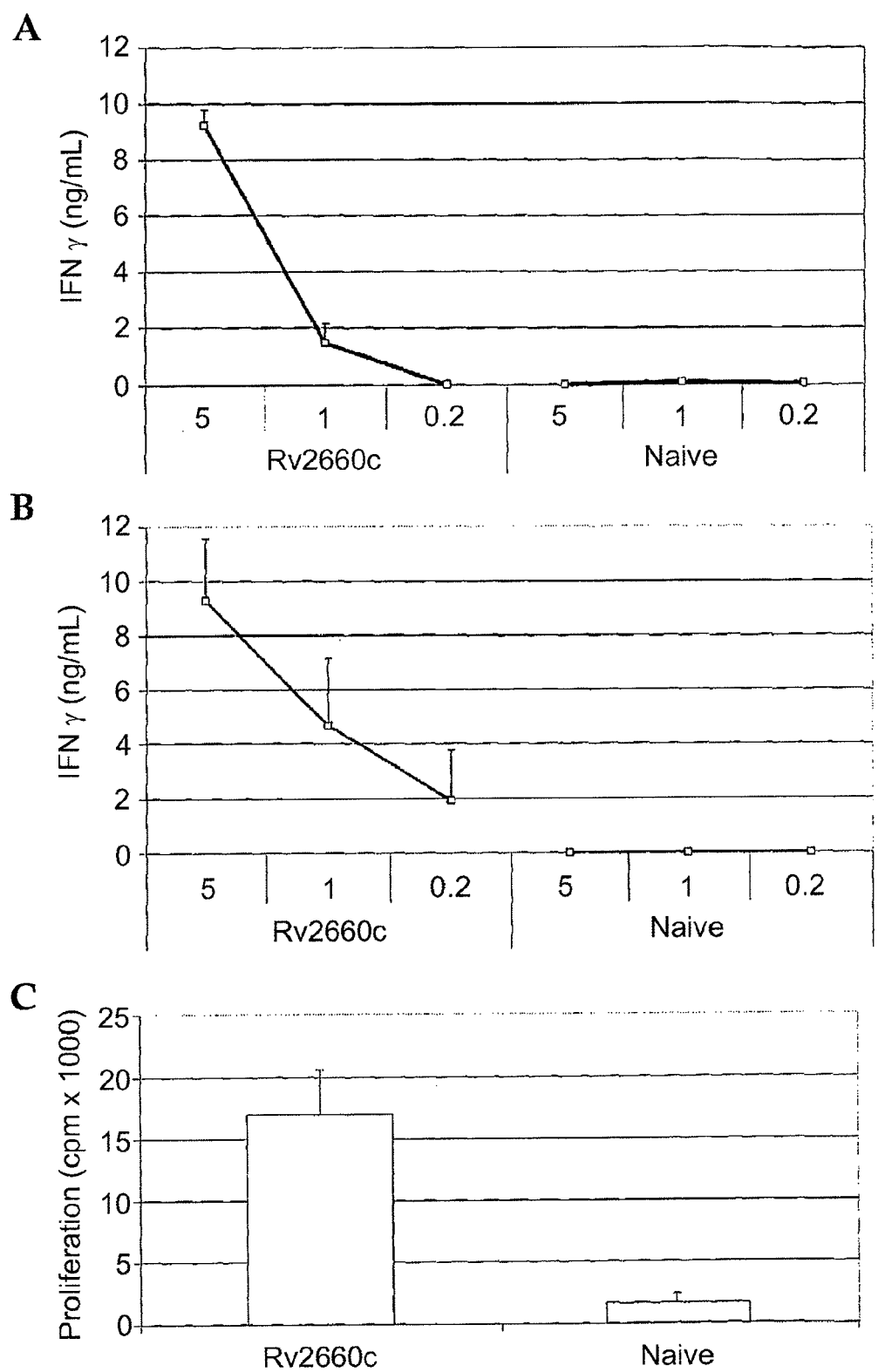

Immunogenicity and Protection Against Aerosol *M. tuberculosis* Infection by the Starvation Induced Antigen Rv2660c Mice were vaccinated three times at two-week intervals with Rv2660c in adjuvant (e.g. DDA/MPL). One week after the final vaccination, blood cells are analyzed by ELISA for IFN-gamma secretion following stimulation with Rv2660c (FIG. 4A). Three weeks after final vaccination spleen cells are analyzed for IFN-gamma secretion following stimulation with Rv2660c (FIG. 4B) and blood cells are analyzed for antigen specific proliferative responses (FIG. 4C).

Figure 5:
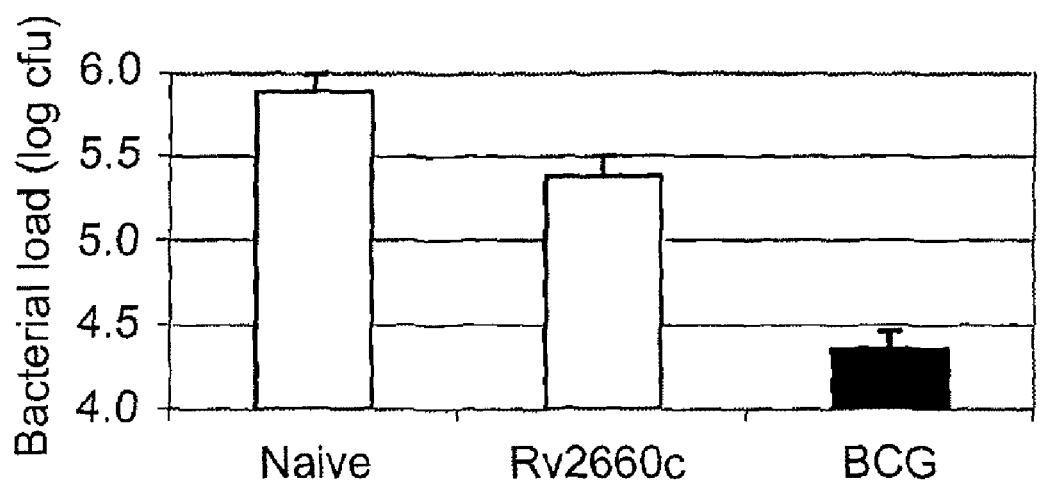

Groups of mice subcutaneously vaccinated three times at two-week intervals with Rv2660c formulated in adjuvant (e.g. DDA/MPL) were challenged by aerosol infection with *M. tuberculosis* and the protective efficacy was assessed by reduction in colony forming units (CFU) isolated from lungs when compared to non-vaccinated mice. Protection was evaluated 12 weeks after vaccination. Rv2660c induced ½ $\log_{10}$ reduction in pulmonary bacterial levels compared to unimmunized infected mice (FIG. 5).

Conclusion

In this study, the potential of a starvation induced protein, Rv2660c as a vaccine antigen was tested. When the Rv2660c protein was administered to mice in the adjuvant combination dimethyldioctadecylammonium bromide-monophosphoryl lipid A, a strong immune response was induced. The immunization resulted in approximately 0.5 $\log_{10}$ reduction in the bacterial burden in the lung.

K. Example 4

Figure 6:
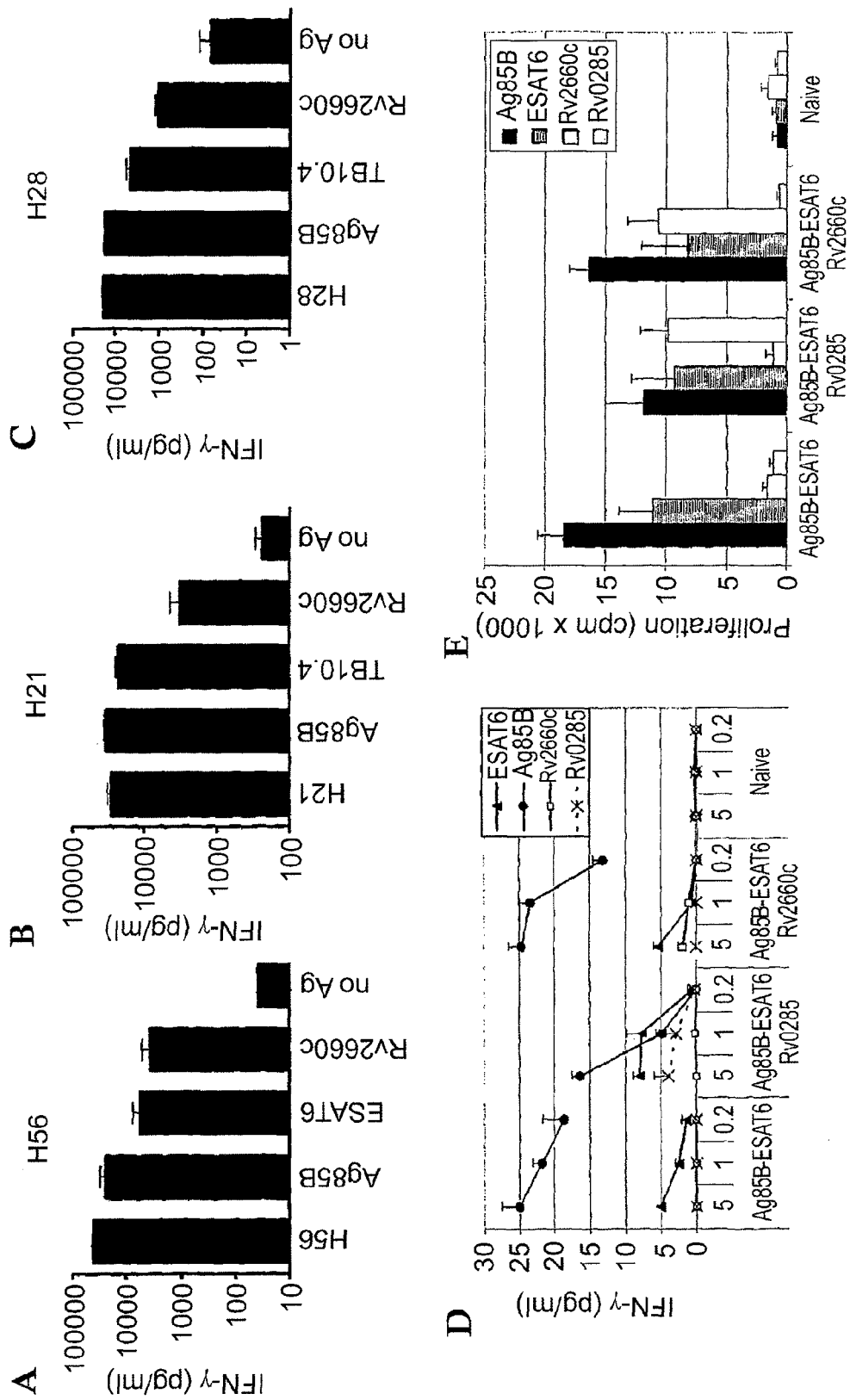

Fusion of Starvation Induced Antigens to Preventive Vaccines (Multiphase Vaccine) Immunological Responses after Immunization with Triple Fusion Proteins Groups of mice are subcutaneously vaccinated two times at two-week intervals with the fusion polypeptides Hybrid56, HyVac21 or HyVac28 in adjuvant (e.g. DDA/MPL). One week after the final vaccination, blood cells are analyzed for IFN-gamma secretion following stimulation with 1 microgram/ml immunization fusion protein or the single components in the fusion proteins (FIG. 6A-C). Three weeks after the final vaccination with Hybrid56, PBMCs are analyzed by ELISA for IFN-gamma secretion following stimulation with 1 microgram/ml of the single components in the fusion protein (FIG. 6D). Alternatively, spleen cells are analyzed for antigen specific proliferative responses three weeks after final vaccination (FIG. 6E), The Ability of Three Fusion Polypeptides to Induce Protection Against Infection with *M. tuberculosis* in Mice Groups of mice are subcutaneously vaccinated three times at two-week intervals with the fusion polypeptides Hybrid1, Hybrid56 and Hybrid32 in adjuvant (DDA/MPL) and protective efficacy are assessed by reduction in colony forming units (CFU) from lungs and spleens when compared to naïve (non-vaccinated) mice after aerosol infection. As a positive control for protection, a single dose of BCG Danish 1331 (5×10$^4$ bacilli/mouse) is injected s.c. at the base of the tail at the same time as the first subunit vaccination (FIGS. 7A and B).

Protective Ability of the Polypeptide Hybrid56 (Ag85b-ESAT6-Rv2660c) Against an Aerosol *M. tuberculosis* Infection in Guinea Pigs Groups of guinea pigs are subcutaneously vaccinated three times at three-week intervals with the fusion polypeptide in adjuvant (e.g. DDA/MPL) and protective efficacy are primarily assessed by measuring each animals weigh on a weekly basis. As a positive control for protection, a single dose of BCG Danish 1331 (5×10$^4$ bacilli/mouse) is injected i.d. at the same time as the first subunit vaccination. Results are presented as survival curves in FIG. 8.

Conclusion

In this study the immunological potential of three fusion proteins (Hybrid56, HyVac21 and HyVac28) were investigated. When the fusion proteins were administered to mice in the adjuvant combination dimethyl dioctadecylammonium bromide-monophosphoryl lipid A, a strong dose-dependent immune response was induced to all three single protein components indicating its potential as a multi-phase vaccine. Selecting Hybrid56 as an example the immune responses induced were accompanied by high levels of protective immunity that increase with time, reaching a level that was clearly above the protection level reached with *Mycobacterium bovis* BCG, the classical MTB vaccine. Further, a similar triple fusion protein containing the classical MTB latency antigen Rv2031c (Ag85B-ESAT6-Rv2031c replacing Rv2660c, did not show improved protection over time. Finally, the high level of protection for Hybrid56 was confirmed in the much more susceptible guinea pig model.

L. Example 5

Activity of a Fusion of a Starvation Induced Antigen and a Preventive Vaccine (Multiphase Vaccine) Administered Post Exposure (Therapeutically).

Mice were infected with *M. tuberculosis* and treated with antibiotics to reduce the bacterial burden and enter a stage of latent infection with a low bacterial burden. During the latent stage of infection the mice were vaccinated three times at two-week intervals with the fusion polypeptide in adjuvant (e.g. DDA/MPL). Fifteen weeks after the final vaccination, blood cells are analyzed by ELISA for IFN-gamma secretion following stimulation with 0.2, 1, or 5 ug/ml of single components of the fusion protein. (FIG. 9A).

The Ability of the Fusion Polypeptide to Induce Protection Against Reactivation of *M. tuberculosis*

Groups of mice with latent *M. tuberculosis* were subcutaneously vaccinated three times at two-week intervals with the fusion polypeptide formulated in adjuvant (e.g. DDA/MPL) and protective efficacy were assessed by reduction in colony forming units (CFU) from lungs when compared to non-vaccinated (latently infected) mice. Protection against reactivation was evaluated three months after vaccination. The fusion polypeptide induced a significant reduction of reactivation resulting in reduced pulmonary bacterial levels compared to reactivated unimmunized latently infected mice (FIG. 9B).

Conclusion

In this study, the potential of a *tuberculosis* subunit vaccine based on a fusion protein of the antigens Rv2660c, ESAT6 (Rv3875) and antigen 85B (Rv1886c) as a therapeutic vaccine was investigated. When fusion protein was administered to mice in the adjuvant combination dimethyldioctadecylammonium bromide-monophosphoryl lipid A, a strong immune response was induced/boosted. The immunization resulted in a reduction in the bacterial burden in the lung during reactivation of latent infection. Thus our studies suggest that post-exposure vaccination with fusion of a starvation induced antigen and a preventive vaccine (Multiphase vaccine) reduces or delays reactivation of *M. tuberculosis*.

REFERENCES

Andersen, P., and Heron, I. 1993 J. Immunol. Methods 161 29-39

Andersen, P. et al 1991. Infect. Immun. 59:1905-1910

Betts J. C. et al 2002. Mol Microbiol. 43:717-731

Brandt, L., et al. 2000 Infect. Immun. 68:2; 791-795.

Brooks, J. V., Frank, A. A., Keen, M. A., Bellisle, J. T. & Orme, I. M. Infect Immun 2001, 69(4), 2714-2717.
Colditz, G. A., Brewer, T. F., Berkey, C. S. et al. JAMA 1994, 271, 698-702
Cole, S. T et al 1998 Nature 393: 537-544
Cote-Siena J, et al 1998, Gene October 9; 221(1):25-34
Gosselin et al., (1992) J. Immunol. 149: 3477-3481
Harboe, M., et al 1998 Infect. Immun. 66:2; 717-723
Honer zu Bentrup, K., Russell, D. G. 2001, Trends Microbiol. 9(12): 597-605
Lowry, D. B. et al 1999, Nature 400: 269-71
Lyashchenko, K. P., et al 2000. J Immunological Methods 242: 91-100
Nagai et al 1991, Infect. Immun 59:1; 372-382
Danish Patent application PA 2000 00666 "Nucleic acid fragments and polypeptide fragments derived from *M. tuberculosis*"
Danish Patent application PA 1999 01020 (WO 01/23388) "*Tuberculosis* vaccine and diagnostic based on the *Mycobacterium tuberculosis* esat-6 gene family".
patent application U.S. Ser. No. 09/0505,739 "Nucleic acid fragments and polypeptide fragments derived from *M. tuberculosis*"
Pollock. J., et al, 2000. The Veterinary record, 146:659-665
Rolph, M. S, and I. A. Ramshaw. 1997. Curr. Opin. Immunol.9:517-24
Rosenkrands, I., et al 1998, Infect. Immun 66:6; 2728-2735
Sambrook et al Molecular Cloning; A laboratory manual, Cold Spring Harbor Laboratories, NY, 1989
Sherman, D. R. et al. 2001 Proc Natl Acad Sci USA 98: 7534-7539
Skjøt, R. L. V., et al 2000, Infect. Immun 68:1; 214-220
Stryhn, A., et al 1996 Eur. J. Immunol. 26:1911-1918
Thompson J., et al Nucleic Acids Res 1994 22:4673-4680
Ulmer J. B et al 1993, Curr. Opin. Invest. Drugs 2(9): 983-989
Olsen A. W et al, Eur J Immunol. 2000 June; 30(6):1724-32
Olsen, A. W., L. A. van Pinxteren, et al. (2001) Infect Immun 69(5): 2773-8.
Theisen, M., J. Vuust, et al. (1995) Clin Diagn Lab Immunol 2(1): 30-4.
Ravn, P. et al 1999. J. Infect. Dis. 179:637-645
Kilgus J et al, J Immunol. 1991 Jan. 1; 146(1):307-15
Sinigaglia F et al. Nature 1988 Dec. 22-29; 336(6201):778-80
Pearson W. R and D. J. Lipman (1988) PNAS USA 85:2444-2448
Kohler and Milstein, Nature, 256:495 (1975)
McCafferty et al, Nature, 348:552-554 (1990)
Merrifield, R. B. Fed. Proc. Am. Soc. Ex. Biol. 21: 412, 1962 and J. Am. Chem. Soc. 85: 2149, 1963
Mowat et al 1991, Immunology 72(3):317-22
Lustig et al 1976, Cell Immunol 24(1):164-72

What is claimed is:

1. An immunogenic composition comprising a fusion polypeptide that comprises at least 8 consecutive amino acids of SEQ ID NO: 12.

2. The immunogenic composition according to claim 1, wherein said fusion polypeptide further comprises ESAT6, Ag85B, TB10.4 or Ag85A; or
any two or more of ESAT6, Ag85B, TB10.4 or Ag85A.

3. The immunogenic composition according to claim 1, wherein said immunogenic composition is formulated for intradermal, transdermal, subcutaneous, intramuscular, or mucosal delivery.

4. The immunogenic composition according to claim 2, wherein the fusion polypeptide comprises 2 different immunogenic polypeptides.

5. The immunogenic composition according to claim 2, wherein the fusion polypeptide comprises 3 different immunogenic polypeptides.

6. The immunogenic composition according to claim 2, wherein the fusion polypeptide comprises 4 different immunogenic polypeptides.

7. The immunogenic composition according to claim 1, wherein the fusion polypeptide comprises an amino acid sequence selected from the group consisting of:
Ag85B-ESAT6-Rv2660c;
Ag85B-TB10.4-Rv2660c;
Ag85B-Rv2660c;
Ag85A-Rv2660c;
Ag85A-ESAT6-Rv2660c;
Ag85A-TB10.4-Rv2660c;
Rv2660c-Rv2659c; and
Ag85B-ESAT6-Rv2660c-Rv2659c; or
any two or more of:
Ag85B-ESAT6-Rv2660c;
Ag85B-TB10.4-Rv2660c;
Ag85B-Rv2660c;
Ag85A-Rv2660c;
Ag85A-ESAT6-Rv2660c;
Ag85A-TB10.4-Rv2660c;
Rv2660c-Rv2659c; or
Ag85B-ESAT6-Rv2660c-Rv2659c.

8. The immunogenic composition of claim 1, further comprising an adjuvant.

9. An immunogenic composition comprising a nucleic acid that comprises a nucleic acid sequence encoding at least 8 consecutive amino acids of SEQ ID NO: 12.

10. The immunogenic composition according to claim 9, wherein said nucleic acid further encodes ESAT6, Ag85B, TB10.4 or Ag85A; or
any two or more of ESAT6, Ag85B, TB10.4 or Ag85A.

11. The immunogenic composition according to claim 9, wherein said immunogenic composition is formulated for intradermal, transdermal, subcutaneous, intramuscular, or mucosal delivery.

12. The immunogenic composition according to claim 10, wherein said nucleic acid encodes at least 2 different immunogenic polypeptides.

13. The immunogenic composition according to claim 10, wherein said nucleic acid encodes at least 3 different immunogenic polypeptides.

14. The immunogenic composition according to claim 10, wherein said nucleic acid encodes at least 4 different immunogenic polypeptides.

15. The immunogenic composition according to claim 9, wherein said nucleic acid encodes at least an amino acid sequence selected from the group consisting of:
Ag85B-ESAT6-Rv2660c;
Ag85B-TB10.4-Rv2660c;
Ag85B-Rv2660c;
Ag85A-Rv2660c;
Ag85A-ESAT6-Rv2660c;
Ag85A-TB10.4-Rv2660c;
Rv2660c-Rv2659c; and
Ag85B-ESAT6-Rv2660c-Rv2659c; or
any two or more of:
Ag85B-ESAT6-Rv2660c;
Ag85B-TB10.4-Rv2660c;
Ag85B-Rv2660c;
Ag85A-Rv2660c;
Ag85A-ESAT6-Rv2660c;
Ag85A-TB10.4-Rv2660c;
Rv2660c-Rv2659c; or
Ag85B-ESAT6-Rv2660c-Rv2659c.

16. The immunogenic composition of claim 9, further comprising an adjuvant.

17. A method of immunizing an animal against tuberculosis comprising administering to said animal the immunogenic composition according to claim 1.

18. A method of immunizing an animal against tuberculosis comprising administering to said animal the immunogenic composition according to claim 9.

* * * * *

```
SEQUENCE LISTING

<160> NUMBER OF SEQ ID NOS: 18

<210> SEQ ID NO 1
<211> LENGTH: 960
<212> TYPE: DNA
<213> ORGANISM: Mycobacterium tuberculosis

<400> SEQUENCE: 1
atggctgaca tcccctacgg ccgtgactat cccgacccga tctggtgtga cgaggacggc      60
cagccgatgc cgccggtcgg cgccgaattg ctcgacgaca ttagggcatt cttgcggcgg     120
ttcgtagtct atccaagcga ccatgaactg atcgcgcaca ccctctggat tgcgcattgc     180
tggtttatgg aggcgtggga ctcaacgccc cgaatcgctt ttttgtcacc ggaacccggc     240
tctggcaaga gccgcgcact cgaagtcacg gaaccgctag tgccccggcc ggtgcatgcc     300
atcaactgca caccggccta cctgttccgt cgggtggccg atccggtcgg gcggccgacc     360
gtcctgtacg acgagtgtga caccctgttt ggcccgaaag ctaaagaaca cgaggaaatt     420
cgcggcgtga tcaacgccgg ccaccgcaag ggagccgtcg cgggccgctg cgtcatccgc     480
ggcaagatcg ttgagaccga ggaactgcca gcgtactgtg cggtcgcctt ggccggcctc     540
gacgacctgc ccgacaccat catgtctcgg tcgatcgtgg tgaggatgcg caggagggca     600
ccaaccgaac ccgtggagcc gtggcgcccc cgcgtcaacg gccccgaggc cgagaagctg     660
cacgaccggt tggcgaactg ggcggccgcc attaacccgc tggaaagcgg ttggccggcg     720
atgccggacg gggtgaccga ccggcgcgcc gacgtctggg agtccctggt tgcggttgct     780
gacaccgcgg gcgggcactg gcccaaaacc gcccgtgcaa ccgcagaaac ggatgcaacc     840
gcaaatcgag gagccaagcc cagcataggc gtgctgctgc tgcgggatat ccgtcgagtc     900
ttcagcgacc gggaccggat gcgcaccagc gacatcctga ccggactgaa ccggatggag     960

<210> SEQ ID NO 2
<211> LENGTH: 475
```

-continued

```
<212> TYPE: PRT
<213> ORGANISM: Mycobacterium tuberculosis

<400> SEQUENCE: 2

Met Ala Asp Ile Pro Tyr Gly Arg Asp Tyr Pro Asp Pro Ile Trp Cys
1               5                   10                  15

Asp Glu Asp Gly Gln Pro Met Pro Val Gly Ala Glu Leu Leu Asp
            20                  25                  30

Asp Ile Arg Ala Phe Leu Arg Arg Phe Val Val Tyr Pro Ser Asp His
        35                  40                  45

Glu Leu Ile Ala His Thr Leu Trp Ile Ala His Cys Trp Phe Met Glu
    50                  55                  60

Ala Trp Asp Ser Thr Pro Arg Ile Ala Phe Leu Ser Pro Glu Pro Gly
65                  70                  75                  80

Ser Gly Lys Ser Arg Ala Leu Glu Val Thr Glu Pro Leu Val Pro Arg
                85                  90                  95

Pro Val His Ala Ile Asn Cys Thr Pro Ala Tyr Leu Phe Arg Arg Val
            100                 105                 110

Ala Asp Pro Val Gly Arg Pro Thr Val Leu Tyr Asp Glu Cys Asp Thr
        115                 120                 125

Leu Phe Gly Pro Lys Ala Lys Glu His Glu Glu Ile Arg Gly Val Ile
    130                 135                 140

Asn Ala Gly His Arg Lys Gly Ala Val Ala Gly Arg Cys Val Ile Arg
145                 150                 155                 160

Gly Lys Ile Val Glu Thr Glu Glu Leu Pro Ala Tyr Cys Ala Val Ala
                165                 170                 175

Leu Ala Gly Leu Asp Asp Leu Pro Asp Thr Ile Met Ser Arg Ser Ile
            180                 185                 190

Val Val Arg Met Arg Arg Ala Pro Thr Glu Pro Val Glu Pro Trp
        195                 200                 205

Arg Pro Arg Val Asn Gly Pro Glu Ala Glu Lys Leu His Asp Arg Leu
    210                 215                 220

Ala Asn Trp Ala Ala Ala Ile Asn Pro Leu Glu Ser Gly Trp Pro Ala
225                 230                 235                 240

Met Pro Asp Gly Val Thr Asp Arg Arg Ala Asp Val Trp Glu Ser Leu
                245                 250                 255

Val Ala Val Ala Asp Thr Ala Gly Gly His Trp Pro Lys Thr Ala Arg
            260                 265                 270

Ala Thr Ala Glu Thr Asp Ala Thr Ala Asn Arg Gly Ala Lys Pro Ser
        275                 280                 285

Ile Gly Val Leu Leu Leu Arg Asp Ile Arg Arg Val Phe Ser Asp Arg
    290                 295                 300

Asp Arg Met Arg Thr Ser Asp Ile Leu Thr Gly Leu Asn Arg Met Glu
305                 310                 315                 320

Glu Gly Pro Trp Gly Ser Ile Arg Gly Asp Pro Leu Asp Ala Arg
                325                 330                 335

Gly Leu Ala Thr Arg Leu Gly Arg Tyr Gly Ile Gly Pro Lys Phe Gln
            340                 345                 350

His Ser Gly Gly Glu Pro Pro Tyr Lys Gly Tyr Ser Arg Thr Gln Phe
        355                 360                 365

Glu Asp Ala Trp Ser Arg Tyr Leu Ser Ala Asp Glu Thr Pro Glu
    370                 375                 380

Glu Arg Asp Leu Ser Val Ser Ala Val Ser Ala Val Ser Pro Pro Val
385                 390                 395                 400
```

```
Gly Asp Pro Gly Asp Ala Thr Gly Ala Thr Asp Ala Thr Asp Leu Pro
            405                 410                 415

Glu Ala Gly Asp Leu Pro Tyr Glu Pro Pro Ala Pro Asn Gly His Pro
            420                 425                 430

Asn Gly Asp Ala Pro Leu Cys Ser Gly Pro Gly Cys Pro Asn Lys Leu
            435                 440                 445

Leu Ser Thr Glu Ala Lys Ala Ala Gly Lys Cys Arg Pro Cys Arg Gly
450                 455                 460

Arg Ala Ala Ala Ser Ala Arg Asp Gly Ala Arg
465                 470                 475

<210> SEQ ID NO 3
<211> LENGTH: 393
<212> TYPE: DNA
<213> ORGANISM: Mycobacterium tuberculosis

<400> SEQUENCE: 3
atgaccgccg tcggcgggtc gccgccgacg cgacgatgcc cggccacaga ggaccgggca      60
cccgcgacag tcgccacacc gtctagcacc gatcctaccg cgtcccgcgc cgtgtcgtgg     120
tggtcggtgc acgagtatgt cgcaccgacc ctggccgccg ccgtggaatg ccgatggcc     180 ggcaccccgg cgtggtgcga cctcgacgac accgacccgg tcaaatgggc cgcgatctgc     240
gacgctgctc ggcattgggc actccgggtg agacgtgcc aggccgcgtc ggccgaggca      300
tcacgtgacg tatccgccgc cgccgactgg ccggcggtct ctcgggagat ccagcgtcgg     360
cgtgacgcct acattcggcg ggtggtggtc tga                                  393

<210> SEQ ID NO 4
<211> LENGTH: 130
<212> TYPE: PRT
<213> ORGANISM: Mycobacterium tuberculosis

<400> SEQUENCE: 4

Met Thr Ala Val Gly Gly Ser Pro Pro Thr Arg Arg Cys Pro Ala Thr
1               5                   10                  15

Glu Asp Arg Ala Pro Ala Thr Val Ala Thr Pro Ser Ser Thr Asp Pro
            20                  25                  30

Thr Ala Ser Arg Ala Val Ser Trp Trp Ser Val His Glu Tyr Val Ala
        35                  40                  45

Pro Thr Leu Ala Ala Ala Val Glu Trp Pro Met Ala Gly Thr Pro Ala
    50                  55                  60

Trp Cys Asp Leu Asp Asp Thr Asp Pro Val Lys Trp Ala Ala Ile Cys
65                  70                  75                  80

Asp Ala Ala Arg His Trp Ala Leu Arg Val Glu Thr Cys Gln Ala Ala
                85                  90                  95

Ser Ala Glu Ala Ser Arg Asp Val Ser Ala Ala Ala Asp Trp Pro Ala
            100                 105                 110

Val Ser Arg Glu Ile Gln Arg Arg Asp Ala Tyr Ile Arg Arg Val
        115                 120                 125

Val Val
    130

<210> SEQ ID NO 5
<211> LENGTH: 261
<212> TYPE: DNA
<213> ORGANISM: Mycobacterium tuberculosis

<400> SEQUENCE: 5
```

```
atgtgcgcgt tcccgtcgcc gagtctcggg tggacggtct ctcacgagac cgaaaggccc    60
ggcatggcag acgctccccc gttgtcacgg cggtacatca cgatcagtga ggccgccgaa   120
tatctagcgg tcaccgaccg cacggtccgc cagatgatcg ccgacggccg cctacgcgga   180
taccgctccg gcacccgcct cgtccgtctg cgccgcgatg aggtcgacgg cgccatgcac   240
ccgttcggtg gtgccgcatg a                                             261
```

<210> SEQ ID NO 6
<211> LENGTH: 86
<212> TYPE: PRT
<213> ORGANISM: Mycobacterium tuberculosis

<400> SEQUENCE: 6

```
Met Cys Ala Phe Pro Ser Pro Ser Leu Gly Trp Thr Val Ser His Glu
  1               5                  10                  15

Thr Glu Arg Pro Gly Met Ala Asp Ala Pro Pro Leu Ser Arg Arg Tyr
                 20                  25                  30

Ile Thr Ile Ser Glu Ala Ala Glu Tyr Leu Ala Val Thr Asp Arg Thr
             35                  40                  45

Val Arg Gln Met Ile Ala Asp Gly Arg Leu Arg Gly Tyr Arg Ser Gly
         50                  55                  60

Thr Arg Leu Val Arg Leu Arg Arg Asp Glu Val Asp Gly Ala Met His
 65                  70                  75                  80

Pro Phe Gly Gly Ala Ala
                 85
```

<210> SEQ ID NO 7
<211> LENGTH: 363
<212> TYPE: DNA
<213> ORGANISM: Mycobacterium tuberculosis

<400> SEQUENCE: 7

```
atggccgatg cggttaagta cgtagttatg tgcaactgcg acgacgaacc gggagcgctc    60
atcatcgcct ggatcgacga cgaacgaccc gccggcgggc acatacagat gcggtcgaac   120
acccgcttca ccgaaacaca gtggggccgc catatcgagt ggaaactcga atgccgggca   180
tgccgaaagt atgcgccgat atccgagatg accgccgcgg cgatcctcga cggtttcggg   240
gcgaagcttc acgagctgag aacgtcgacc atccccgacg ctgacgatcc atcaatagca   300
gaggcgcgac acgtaattcc gttcagcgca ttatgcttgc gcttgagcca gctaggcggg   360
taa                                                                 363
```

<210> SEQ ID NO 8
<211> LENGTH: 120
<212> TYPE: PRT
<213> ORGANISM: Mycobacterium tuberculosis

<400> SEQUENCE: 8

```
Met Ala Asp Ala Val Lys Tyr Val Val Met Cys Asn Cys Asp Asp Glu
  1               5                  10                  15

Pro Gly Ala Leu Ile Ile Ala Trp Ile Asp Asp Glu Arg Pro Ala Gly
                 20                  25                  30

Gly His Ile Gln Met Arg Ser Asn Thr Arg Phe Thr Glu Thr Gln Trp
             35                  40                  45

Gly Arg His Ile Glu Trp Lys Leu Glu Cys Arg Ala Cys Arg Lys Tyr
         50                  55                  60

Ala Pro Ile Ser Glu Met Thr Ala Ala Ala Ile Leu Asp Gly Phe Gly
 65                  70                  75                  80
```

Ala Lys Leu His Glu Leu Arg Thr Ser Thr Ile Pro Asp Ala Asp
            85                  90                  95

Pro Ser Ile Ala Glu Ala Arg His Val Ile Pro Phe Ser Ala Leu Cys
            100                 105                 110

Leu Arg Leu Ser Gln Leu Gly Gly
            115                 120

<210> SEQ ID NO 9
<211> LENGTH: 1128
<212> TYPE: DNA
<213> ORGANISM: Mycobacterium tuberculosis

<400> SEQUENCE: 9

```
gtgacgcaaa ccggcaagcg tcagagacgc aaattcggtc gcatccgaca gttcaactcc      60
ggccgctggc aagccagcta caccggcccc gacggccgcg tgtacatcgc ccccaaaacc     120
ttcaacgcca agatcgacgc cgaagcatgg ctcaccgacc gccgccgcga aatcgaccga     180
caactatggt ccccggcatc gggtcaggaa gaccgccccg gagccccatt cggtgagtac     240
gccgaaggat ggctgaagca gcgtggaatc aaggaccgca cccgcgccca ctatcgcaaa     300
ctgctggaca ccacatcct ggccaccttc gctgacaccg acctacgcga catcaccccg     360
gccgccgtgc cgcgctggta cgccaccacc gccgtgggca caccgaccat gcgggcacac     420
tcctacagct tgctgcgcgc aatcatgcag accgccttgg ccgacgacct gatcgactcc     480
aacccctgcc gcatctcagg cgcgtccacc gcccgccgcg tccacaagat caggcccgcc     540
accctcgacg agctggaaac catcaccaaa gccatgcccg acccctacca ggcgttcgtg     600
ctgatggcgg catggctggc catgcgctac ggcgagctga ccgaattacg ccgcaaagac     660
atcgacctgc acggcgaggt tgcgcgggtg cggcgggctg tcgttcgggt gggcgaaggc     720
ttcaaggtga cgacaccgaa aagcgatgcg ggagtgcgcg acataagtat cccgccacat     780
ctgataccccg ccatcgaaga ccaccttcac aaacacgtca accccggccg ggagtccctg     840
ctgttcccat cggtcaacga ccccaaccgt cacctagcac cctcggcgct gtaccgcatg     900
ttctacaagg cccgaaaagc cgccggccga ccagactaca gggtgcacga ccttcgacac     960
tccggcgccg tgttggctgc atccaccggc gccacactgg ccgaactgat gcagcggcta    1020
ggacacagca cagccggcgc cgcactccgc taccagcacg ccgccaaggg ccgggaccgc    1080
gaaatcgccg cactgttaag caaactggcc gagaaccagg agatgtga                1128
```

<210> SEQ ID NO 10
<211> LENGTH: 375
<212> TYPE: PRT
<213> ORGANISM: Mycobacterium tuberculosis

<400> SEQUENCE: 10

Val Thr Gln Thr Gly Lys Arg Gln Arg Arg Lys Phe Gly Arg Ile Arg
1               5                   10                  15

Gln Phe Asn Ser Gly Arg Trp Gln Ala Ser Tyr Thr Gly Pro Asp Gly
                20                  25                  30

Arg Val Tyr Ile Ala Pro Lys Thr Phe Asn Ala Lys Ile Asp Ala Glu
            35                  40                  45

Ala Trp Leu Thr Asp Arg Arg Arg Glu Ile Asp Arg Gln Leu Trp Ser
        50                  55                  60

Pro Ala Ser Gly Gln Glu Asp Arg Pro Gly Ala Pro Phe Gly Glu Tyr
65                  70                  75                  80

Ala Glu Gly Trp Leu Lys Gln Arg Gly Ile Lys Asp Arg Thr Arg Ala

```
                    85                  90                  95
His Tyr Arg Lys Leu Leu Asp Asn His Ile Leu Ala Thr Phe Ala Asp
            100                 105                 110

Thr Asp Leu Arg Asp Ile Thr Pro Ala Ala Val Arg Trp Tyr Ala
        115                 120                 125

Thr Thr Ala Val Gly Thr Pro Thr Met Arg Ala His Ser Tyr Ser Leu
    130                 135                 140

Leu Arg Ala Ile Met Gln Thr Ala Leu Ala Asp Asp Leu Ile Asp Ser
145                 150                 155                 160

Asn Pro Cys Arg Ile Ser Gly Ala Ser Thr Ala Arg Arg Val His Lys
                165                 170                 175

Ile Arg Pro Ala Thr Leu Asp Glu Leu Glu Thr Ile Thr Lys Ala Met
            180                 185                 190

Pro Asp Pro Tyr Gln Ala Phe Val Leu Met Ala Ala Trp Leu Ala Met
        195                 200                 205

Arg Tyr Gly Glu Leu Thr Glu Leu Arg Arg Lys Asp Ile Asp Leu His
    210                 215                 220

Gly Glu Val Ala Arg Val Arg Arg Ala Val Val Arg Val Gly Glu Gly
225                 230                 235                 240

Phe Lys Val Thr Thr Pro Lys Ser Asp Ala Gly Val Arg Asp Ile Ser
                245                 250                 255

Ile Pro Pro His Leu Ile Pro Ala Ile Glu Asp His Leu His Lys His
            260                 265                 270

Val Asn Pro Gly Arg Glu Ser Leu Leu Phe Pro Ser Val Asn Asp Pro
        275                 280                 285

Asn Arg His Leu Ala Pro Ser Ala Leu Tyr Arg Met Phe Tyr Lys Ala
    290                 295                 300

Arg Lys Ala Ala Gly Arg Pro Asp Leu Arg Val His Asp Leu Arg His
305                 310                 315                 320

Ser Gly Ala Val Leu Ala Ala Ser Thr Gly Ala Thr Leu Ala Glu Leu
                325                 330                 335

Met Gln Arg Leu Gly His Ser Thr Ala Gly Ala Ala Leu Arg Tyr Gln
            340                 345                 350

His Ala Ala Lys Gly Arg Asp Arg Glu Ile Ala Ala Leu Leu Ser Lys
        355                 360                 365

Leu Ala Glu Asn Gln Glu Met
    370                 375

<210> SEQ ID NO 11
<211> LENGTH: 228
<212> TYPE: DNA
<213> ORGANISM: Mycobacterium tuberculosis

<400> SEQUENCE: 11
gtgatagcgg gcgtcgacca ggcgcttgca gcaacaggcc aggctagcca gcgggcggca      60
ggcgcatctg gtggggtcac cgtcggtgtc ggcgtgggca cggaacagag gaacctttcg     120
gtggttgcac cgagtcagtt cacatttagt tcacgcagcc cagattttgt ggatgaaacc     180
gcaggtcaat cgtggtgcgc gatactggga ttgaaccagt ttcactag                  228

<210> SEQ ID NO 12
<211> LENGTH: 75
<212> TYPE: PRT
<213> ORGANISM: Mycobacterium tuberculosis

<400> SEQUENCE: 12
```

-continued

```
Val Ile Ala Gly Val Asp Gln Ala Leu Ala Ala Thr Gly Gln Ala Ser
1               5                   10                  15

Gln Arg Ala Ala Gly Ala Ser Gly Gly Val Thr Val Gly Val Gly Val
            20                  25                  30

Gly Thr Glu Gln Arg Asn Leu Ser Val Val Ala Pro Ser Gln Phe Thr
        35                  40                  45

Phe Ser Ser Arg Ser Pro Asp Phe Val Asp Glu Thr Ala Gly Gln Ser
    50                  55                  60

Trp Cys Ala Ile Leu Gly Leu Asn Gln Phe His
65                  70                  75

<210> SEQ ID NO 13
<211> LENGTH: 390
<212> TYPE: DNA
<213> ORGANISM: Mycobacterium tuberculosis

<400> SEQUENCE: 13
atgagggctc gcagcgatgc tggaggccag tctgtgaagt cccgcacgtc gaatcggtcc      60
agaagctcgc gccggagccg cgtcaggtca tccatcagtg ccctcgttga taatccgcag     120
gctcggccgc gcgagctccc tgttctgtgc gggtggcccg tagtgcgcgt cgagccggtc     180
tgcgagttcg tgccggagcc ggtttgtgga caggccgagg tgctcggcga gccagccgcc     240
gctcatcggg tcacctcagc ccgccggtca ccctcaacga ccgtttgcag ccgttcgcag     300
aaggcgagcg cggtggtgat cagctccgtc agctcggttg cgcgggtgcg gcgtgcctcg     360
gtgagttcgg tggacgcgac aacagcgtga                                      390

<210> SEQ ID NO 14
<211> LENGTH: 129
<212> TYPE: PRT
<213> ORGANISM: Mycobacterium tuberculosis

<400> SEQUENCE: 14

Met Arg Ala Arg Ser Asp Ala Gly Gly Gln Ser Val Lys Ser Arg Thr
1               5                   10                  15

Ser Asn Arg Ser Arg Ser Ser Arg Arg Ser Arg Val Arg Ser Ser Ile
            20                  25                  30

Ser Ala Leu Val Asp Asn Pro Gln Ala Arg Pro Arg Glu Leu Pro Val
        35                  40                  45

Leu Cys Gly Trp Pro Val Val Arg Val Glu Pro Val Cys Glu Phe Val
    50                  55                  60

Pro Glu Pro Val Cys Gly Gln Ala Glu Val Leu Gly Glu Pro Ala Ala
65                  70                  75                  80

Ala His Arg Val Thr Ser Ala Arg Arg Ser Pro Ser Thr Thr Val Cys
                85                  90                  95

Ser Arg Ser Gln Lys Ala Ser Ala Val Val Ile Ser Ser Val Ser Ser
            100                 105                 110

Val Ala Arg Val Arg Arg Ala Ser Val Ser Ser Val Asp Ala Thr Thr
        115                 120                 125

Ala

<210> SEQ ID NO 15
<211> LENGTH: 273
<212> TYPE: DNA
<213> ORGANISM: Mycobacterium tuberculosis

<400> SEQUENCE: 15
atggatgacc tgacgcggct ccggcgcgag cttctggacc gattcgacgt gcgggacttc      60
```

```
acagactggc ctccagcatc gctgcgagcc ctcatcgcga cctacgaccc ctggatcgac    120
atgacggcca gcccgccaca gcctgtatcg cccggagggc ctcgactccg actcgtgcga    180
ttaaccacca acccatccgc gagagcagcc cctatcggaa acggtgggga ctcttctgtt    240
tgcgctggtg agaaacagtg ccgcccaccg tag                                 273
```

<210> SEQ ID NO 16
<211> LENGTH: 90
<212> TYPE: PRT
<213> ORGANISM: Mycobacterium tuberculosis

<400> SEQUENCE: 16

```
Met Asp Asp Leu Thr Arg Leu Arg Arg Glu Leu Leu Asp Arg Phe Asp
1               5                   10                  15

Val Arg Asp Phe Thr Asp Trp Pro Ala Ser Leu Arg Ala Leu Ile
            20                  25                  30

Ala Thr Tyr Asp Pro Trp Ile Asp Met Thr Ala Ser Pro Pro Gln Pro
        35                  40                  45

Val Ser Pro Gly Gly Pro Arg Leu Arg Leu Val Arg Leu Thr Thr Asn
    50                  55                  60

Pro Ser Ala Arg Ala Ala Pro Ile Gly Asn Gly Gly Asp Ser Ser Val
65                  70                  75                  80

Cys Ala Gly Glu Lys Gln Cys Arg Pro Pro
                85                  90
```

<210> SEQ ID NO 17
<211> LENGTH: 234
<212> TYPE: DNA
<213> ORGANISM: Mycobacterium tuberculosis

<400> SEQUENCE: 17

```
gtggaggtga gggctagcgc ccgcaagcac ggcatcaacg acgacgccat gctccacgca    60
taccgcaacg cgctgcgcta cgtcgaactg gaataccacg gcgaagttca actgctggtg   120
atcggccccg accaaaccgg cgcctttta gagctggtca tcccagcaga cgaaccaccc   180
cggattatcc acgccaacgt actacgcccg aagttctacg actacctgag gtga         234
```

<210> SEQ ID NO 18
<211> LENGTH: 77
<212> TYPE: PRT
<213> ORGANISM: Mycobacterium tuberculosis

<400> SEQUENCE: 18

```
Val Glu Val Arg Ala Ser Ala Arg Lys His Gly Ile Asn Asp Asp Ala
1               5                   10                  15

Met Leu His Ala Tyr Arg Asn Ala Leu Arg Tyr Val Glu Leu Glu Tyr
            20                  25                  30

His Gly Glu Val Gln Leu Leu Val Ile Gly Pro Asp Gln Thr Gly Arg
        35                  40                  45

Leu Leu Glu Leu Val Ile Pro Ala Asp Glu Pro Arg Ile Ile His
    50                  55                  60

Ala Asn Val Leu Arg Pro Lys Phe Tyr Asp Tyr Leu Arg
65                  70                  75
```